US012599768B2

(12) United States Patent
Carter

(10) Patent No.: US 12,599,768 B2
(45) Date of Patent: Apr. 14, 2026

(54) ADVANCED ELECTRODE DATA ANALYSIS

(71) Applicant: COCHLEAR LIMITED, Macquarie University (AU)

(72) Inventor: Paul Michael Carter, Macquarie University (AU)

(73) Assignee: Cochlear Limited, Macquarie University (AU)

( * ) Notice: Subject to any disclaimer, the term of this patent is extended or adjusted under 35 U.S.C. 154(b) by 1175 days.

(21) Appl. No.: 16/971,283

(22) PCT Filed: Feb. 20, 2019

(86) PCT No.: PCT/IB2019/051345
§ 371 (c)(1),
(2) Date: Aug. 19, 2020

(87) PCT Pub. No.: WO2019/162837
PCT Pub. Date: Aug. 29, 2019

(65) Prior Publication Data
US 2020/0376269 A1 Dec. 3, 2020

Related U.S. Application Data

(60) Provisional application No. 62/633,054, filed on Feb. 20, 2018.

(51) Int. Cl.
*A61N 1/36* (2006.01)
*A61N 1/05* (2006.01)
*H04R 25/00* (2006.01)
(52) U.S. Cl.
CPC ....... *A61N 1/36039* (2017.08); *A61N 1/0541* (2013.01); *H04R 25/603* (2019.05); *H04R 25/70* (2013.01)

(58) Field of Classification Search
CPC .......................... A61N 1/0541; A61N 1/36039
See application file for complete search history.

(56) References Cited

U.S. PATENT DOCUMENTS

| | | | |
|---|---|---|---|
| 8,532,781 | B1 | 9/2013 | Vanpoucke |
| 2007/0270949 | A1 | 11/2007 | Paolini et al. |

(Continued)

FOREIGN PATENT DOCUMENTS

| | | |
|---|---|---|
| EP | 1754509 A1 | 2/2007 |
| KR | 100859979 B1 | 9/2008 |
| WO | 2018173010 A1 | 9/2018 |

OTHER PUBLICATIONS

International Search Report & Written Opinion for PCT/IB2019/051345, mailed Jul. 18, 2019.

(Continued)

*Primary Examiner* — Jennifer Pitrak McDonald
*Assistant Examiner* — Jennifer L Ghand
(74) *Attorney, Agent, or Firm* — Pilloff Passino & Cosenza LLP; Martin J. Cosenza

(57) ABSTRACT

A method, including applying at first and second temporal locations respective electrical currents to an electrode located in a cochlea of a recipient, obtaining first and second data indicative of electrical properties at a plurality of locations away from the electrode, the first and second data corresponding to data obtained, respectively, at the first and second temporal locations, evaluating whether or not there is an existence of a temporal change in electrical conductivity between the electrode and the plurality of locations based on the obtained data, and determining whether or not a phenomenon exists inside the cochlea based on the evaluation.

25 Claims, 26 Drawing Sheets

(56)                    References Cited

U.S. PATENT DOCUMENTS

| | | | |
|---|---|---|---|
| 2009/0023976 A1 | 1/2009 | Cho et al. | |
| 2009/0248110 A1 | 10/2009 | Choi et al. | |
| 2011/0087085 A1 | 4/2011 | Tsampazis et al. | |
| 2012/0071957 A1 | 3/2012 | Carter | |
| 2012/0316454 A1 | 12/2012 | Carter | |
| 2013/0204326 A1 | 8/2013 | Vanpoucke | |
| 2015/0112408 A1 | 4/2015 | Kals | |
| 2015/0258337 A1 | 9/2015 | Long et al. | |
| 2015/0314122 A1 | 11/2015 | Kabot et al. | |
| 2016/0059014 A1 | 3/2016 | Johnston et al. | |
| 2016/0059015 A1 | 3/2016 | Risi et al. | |
| 2016/0310738 A1* | 10/2016 | Mauch | A61N 1/36036 |
| 2018/0056058 A1 | 3/2018 | Heasman et al. | |
| 2018/0140829 A1* | 5/2018 | Ramos de Miguel, Sr. | A61N 1/37252 |
| 2018/0280687 A1 | 10/2018 | Carter et al. | |
| 2019/0030323 A1* | 1/2019 | Koka | A61N 1/0541 |
| 2020/0375667 A1* | 12/2020 | Polak | A61N 1/36135 |
| 2021/0093852 A1* | 4/2021 | Heasman | A61N 1/36038 |

OTHER PUBLICATIONS

Phillip Tran et al., "Development of HEATHER for Cochlear Implant Stimulation Using a New Modeling Workflow," IEEE Transactions on Biomedical Engineering, Oct. 22, 2014, pp. 728-735, vol. 62, issue 2.
Extended European search report for Europe Patent Application No. 19 756 616.9, dated Oct. 15, 2021.

* cited by examiner

INSERTION GUIDE TUBE 210

STOP 204

212 DISTAL END

Distal portion

RAMP 206

200

208 STAGING SECTION

203

202

INSERTION GUIDE TUBE 210

STOP 204

212 DISTAL END

Distal portion

RAMP 206

200

208 STAGING SECTION

HANDLE 202

FIG. 3A

ELECTRODE ARRAY
146

ELECTRODE CONTACTS
148

145
ELECTRODE ASSEMBLY

PLANE OF CURVATURE 350

146 ELECTRODE ARRAY

140 ELECTRODE CONTACTS

145 ELECTRODE ASSEMBLY

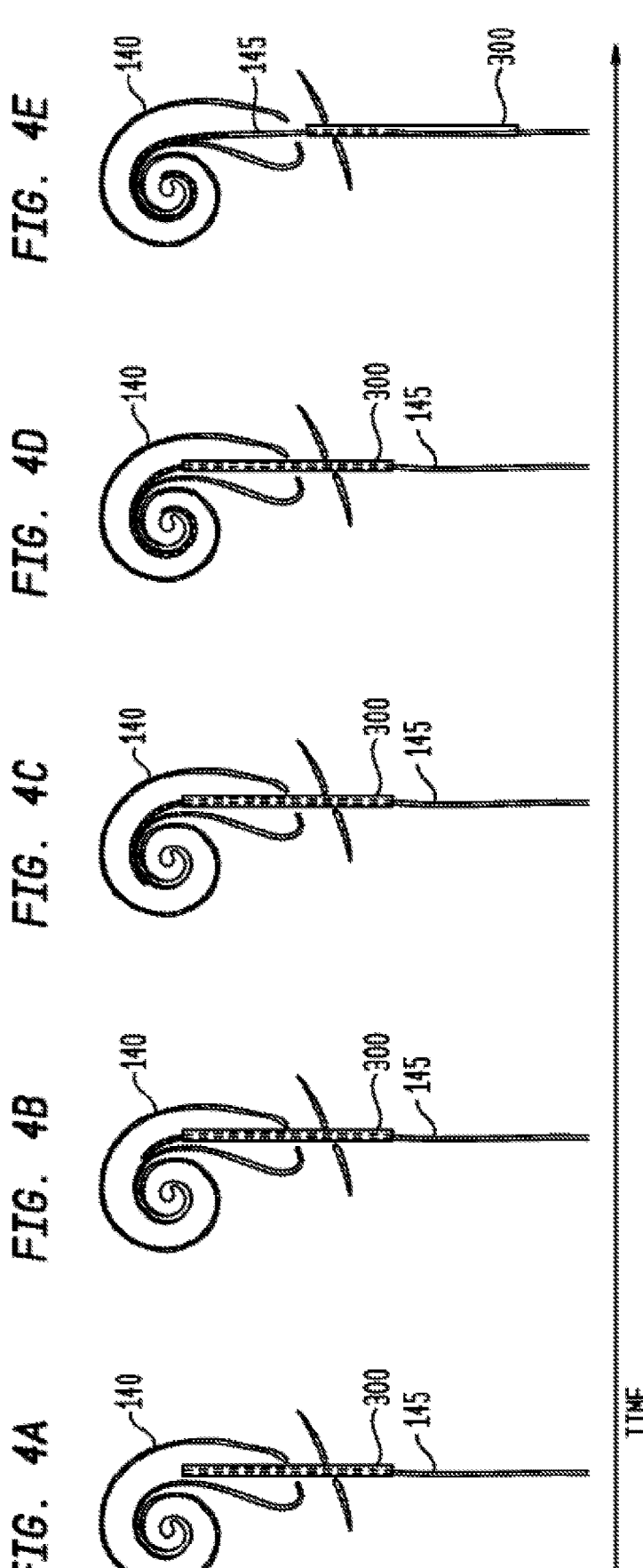

*FIG. 6*

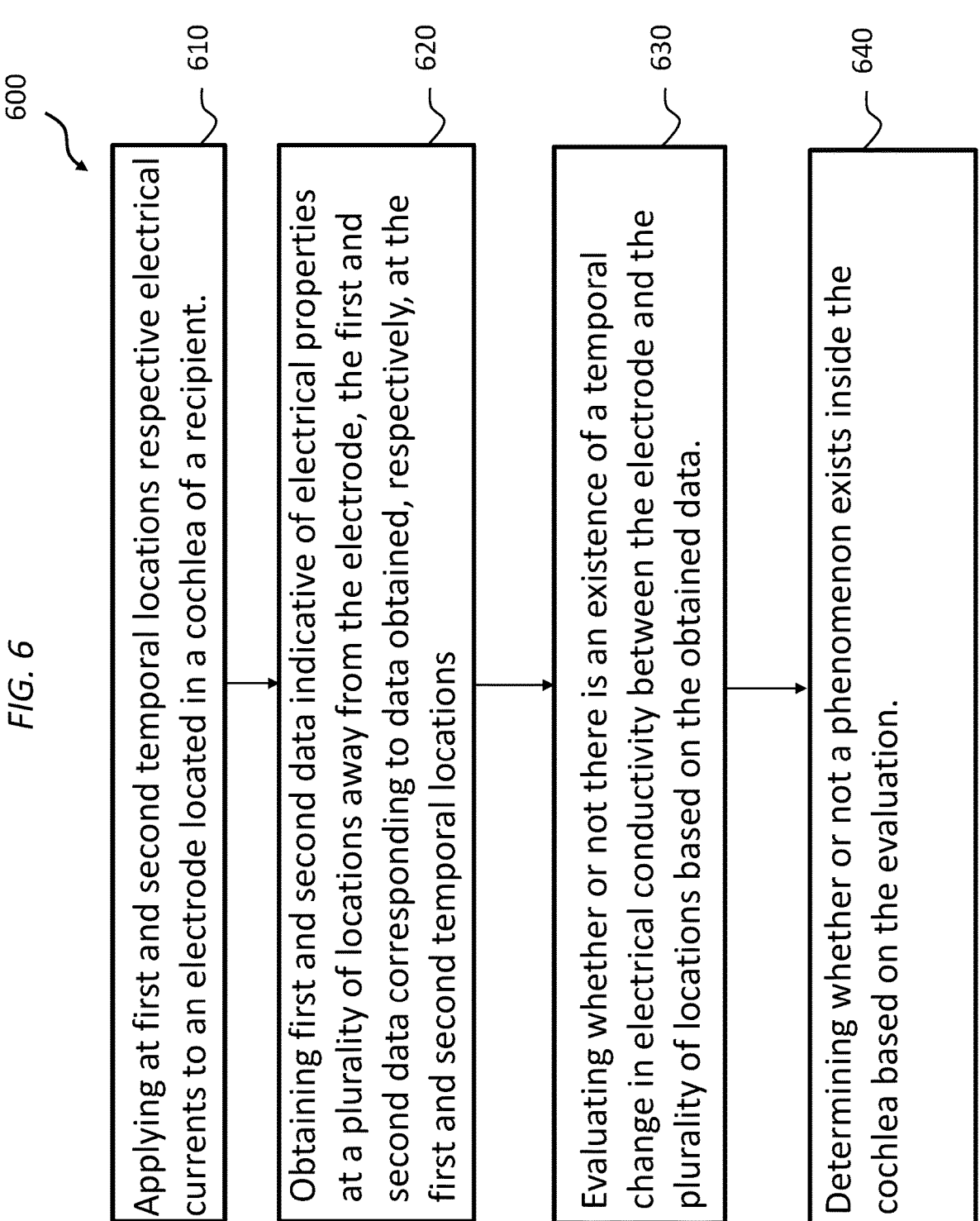

600

610
Applying at first and second temporal locations respective electrical currents to an electrode located in a cochlea of a recipient.

620
Obtaining first and second data indicative of electrical properties at a plurality of locations away from the electrode, the first and second data corresponding to data obtained, respectively, at the first and second temporal locations 630
Evaluating whether or not there is an existence of a temporal change in electrical conductivity between the electrode and the plurality of locations based on the obtained data.

640
Determining whether or not a phenomenon exists inside the cochlea based on the evaluation.

800

810
Executing method 600.

820
Determining that the temporal change has occurred.

830
Determining the temporal length from before a beginning of the change to a point during and/or after the change.

840
Determining that damage has occurred within the cochlea based on the determined temporal length.

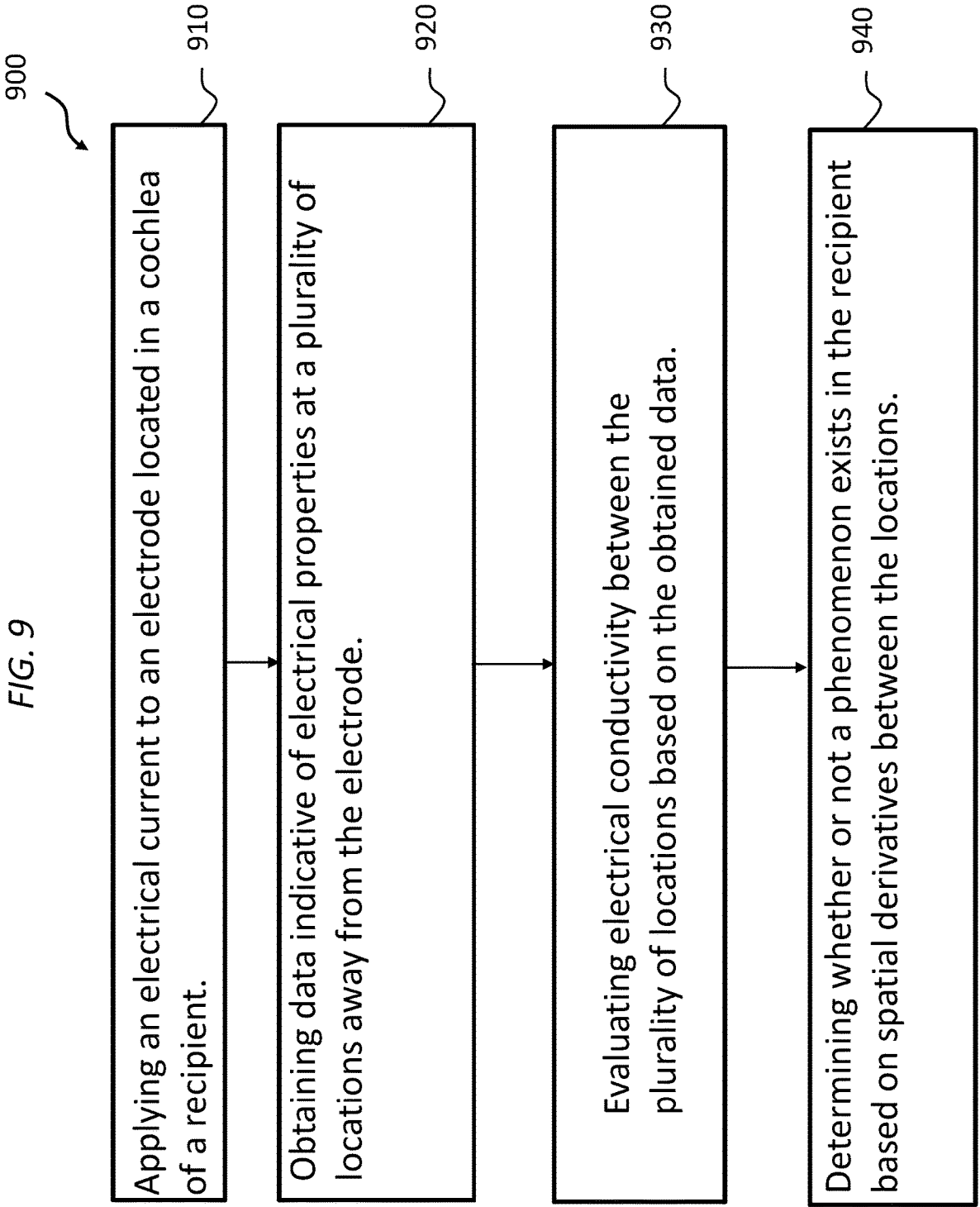

910
Applying an electrical current to an electrode located in a cochlea of a recipient.

920
Obtaining data indicative of electrical properties at a plurality of locations away from the electrode.

930
Evaluating electrical conductivity between the plurality of locations based on the obtained data.

940
Determining whether or not a phenomenon exists in the recipient based on spatial derivatives between the locations.

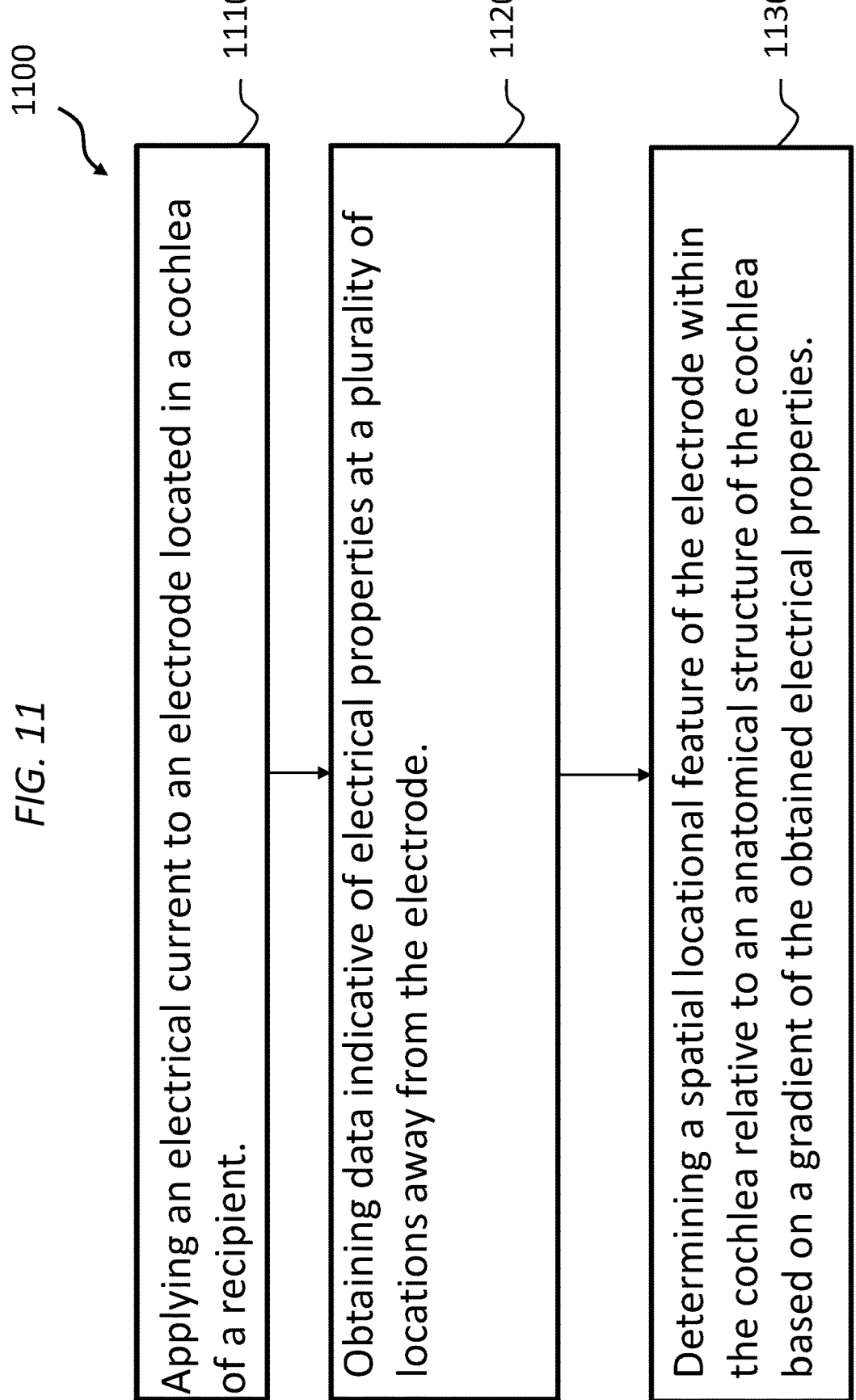

1110
Applying an electrical current to an electrode located in a cochlea of a recipient.

1120
Obtaining data indicative of electrical properties at a plurality of locations away from the electrode.

1130
Determining a spatial locational feature of the electrode within the cochlea relative to an anatomical structure of the cochlea based on a gradient of the obtained electrical properties.

*FIG. 12*

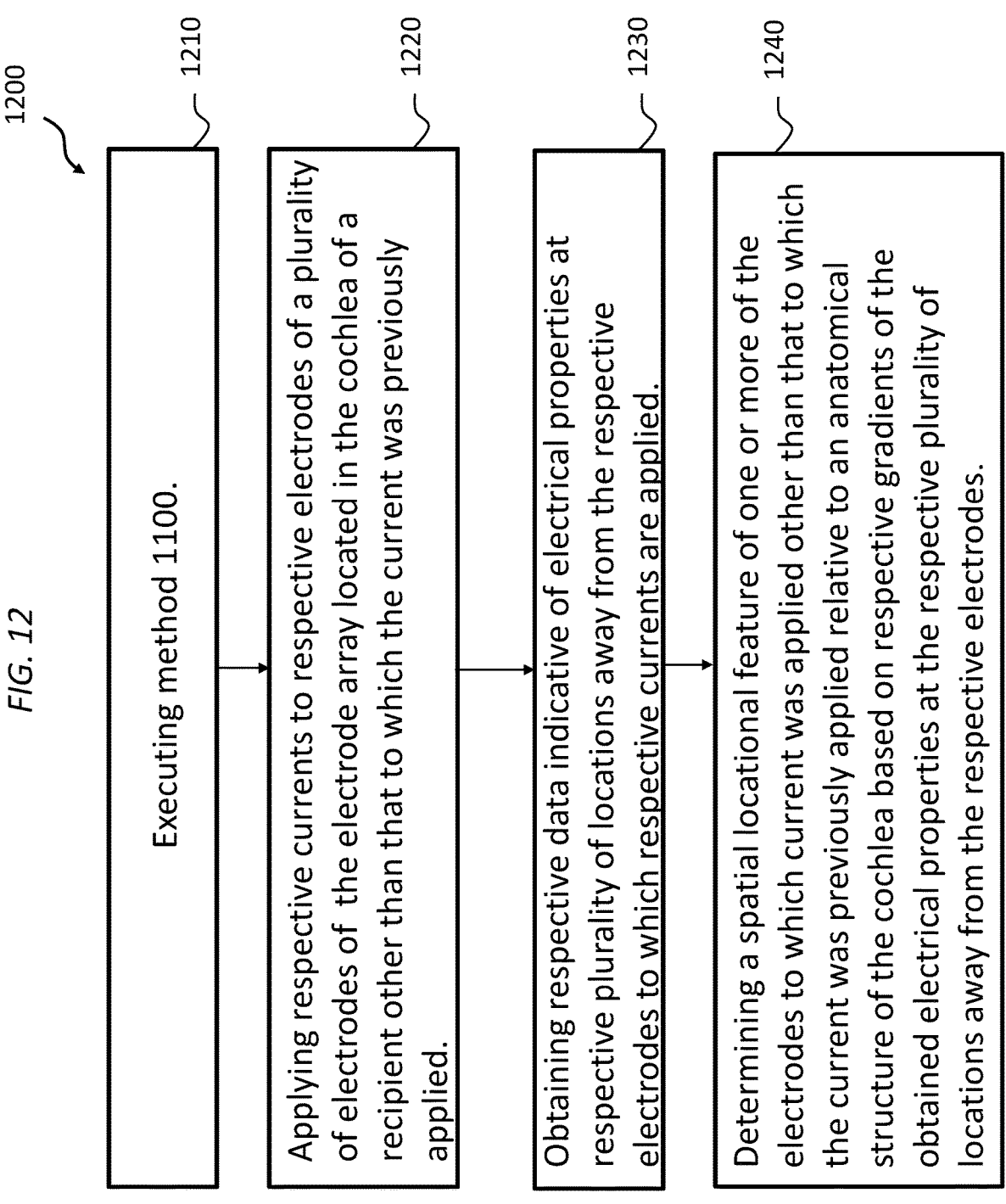

1200

1210

Executing method 1100.

1220

Applying respective currents to respective electrodes of a plurality of electrodes of the electrode array located in the cochlea of a recipient other than that to which the current was previously applied.

1230

Obtaining respective data indicative of electrical properties at respective plurality of locations away from the respective electrodes to which respective currents are applied.

1240

Determining a spatial locational feature of one or more of the electrodes to which current was applied other than that to which the current was previously applied relative to an anatomical structure of the cochlea based on respective gradients of the obtained electrical properties at the respective plurality of locations away from the respective electrodes.

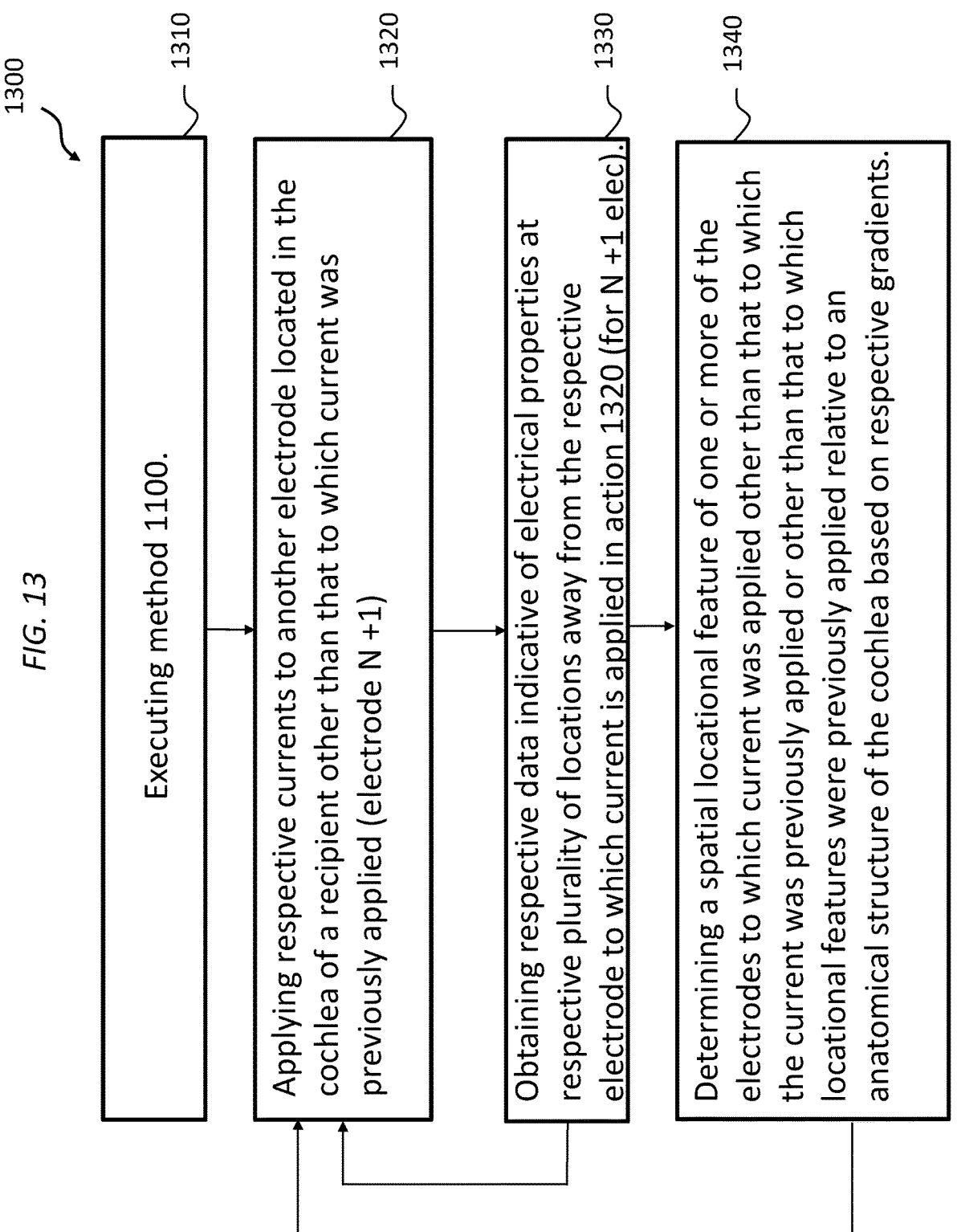

Executing method 1100.

1320

Applying respective currents to another electrode located in the cochlea of a recipient other than that to which current was previously applied (electrode N +1)

1330

Obtaining respective data indicative of electrical properties at respective plurality of locations away from the respective electrode to which current is applied in action 1320 (for N +1 elec).

1340

Determining a spatial locational feature of one or more of the electrodes to which current was applied other than that to which the current was previously applied or other than that to which locational features were previously applied relative to an anatomical structure of the cochlea based on respective gradients.

1400

Applying an electrical current to an electrode located in a cochlea of a recipient for N.
1410

Obtaining data indicative of electrical properties at a plurality of locations away from the electrode N.
1420

Evaluating an electrical feature based on the obtained data.
1430

Learning about a phenomenon in the recipient based on any of the teachings herein.
1440

Figure 16:
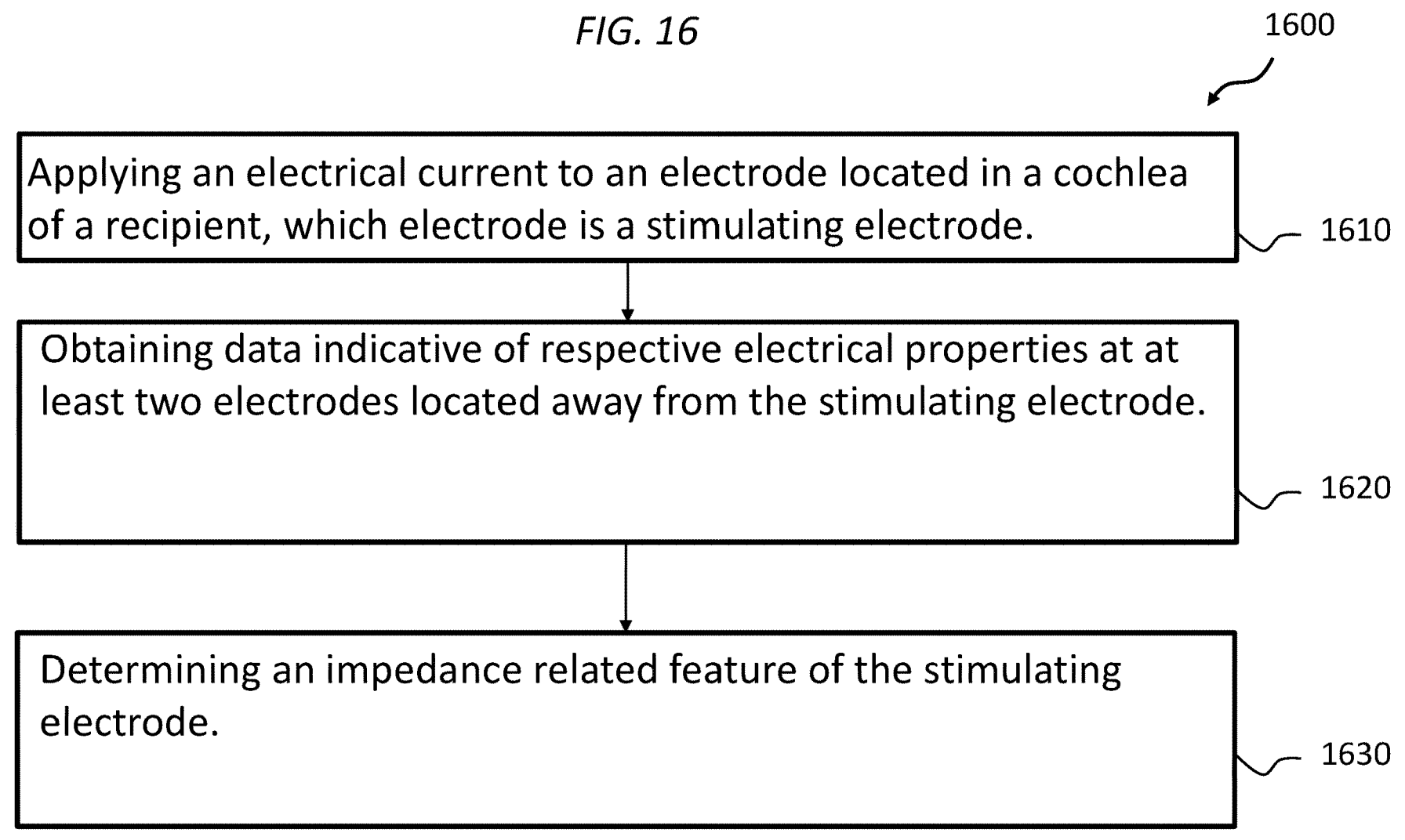

Applying an electrical current to an electrode located in a cochlea of a recipient, which electrode is a stimulating electrode.

1620

Obtaining data indicative of respective electrical properties at at least two electrodes located away from the stimulating electrode.

1630

Determining an impedance related feature of the stimulating electrode.

ADVANCED ELECTRODE DATA ANALYSIS

CROSS-REFERENCE TO RELATED APPLICATIONS

This application claims priority to U.S. Provisional Application No. 62/633,054, entitled ADVANCED ELECTRODE DATA ANALYSIS, filed on Feb. 20, 2018, naming Paul Michael CARTER of Macquarie University, Australia as an inventor, the entire contents of that application being incorporated herein by reference in its entirety.

BACKGROUND

Hearing loss, which may be due to many different causes, is generally of two types: conductive and sensorineural. Sensorineural hearing loss can be due to the absence or destruction of the hair cells in the cochlea that transduce sound signals into nerve impulses. Various hearing prostheses are commercially available to provide individuals suffering from this form of sensorineural hearing loss with the ability to perceive sound. A hearing prosthesis can be a cochlear implant.

Conductive hearing loss occurs when the normal mechanical pathways that provide sound to hair cells in the cochlea are impeded, for example, by damage to the ossicular chain or the ear canal. Individuals suffering from conductive hearing loss may retain some form of residual hearing because the cochlea sensory system may remain undamaged.

Individuals suffering from hearing loss typically receive an acoustic hearing aid. Conventional hearing aids rely on principles of air conduction to transmit acoustic signals to the cochlea. In particular, a hearing aid typically uses an arrangement positioned in the recipient's ear canal or on the outer ear to amplify a sound received by the outer ear of the recipient. This amplified sound reaches the cochlea causing motion of the perilymph and stimulation of the auditory nerve. Cases of conductive hearing loss typically are treated by means of bone conduction hearing aids. In contrast to conventional hearing aids, these devices use a mechanical actuator that is coupled to the skull bone to apply the amplified sound.

In contrast to hearing aids, which rely primarily on the principles of air conduction, certain types of hearing prostheses commonly referred to as cochlear implants convert a received sound into electrical stimulation. The electrical stimulation is applied to the cochlea, which results in the perception of the received sound.

Many devices, such as medical devices that interface with a recipient, have structural and/or functional features where there is utilitarian value in adjusting such features for an individual recipient. The process by which a device that interfaces with or otherwise is used by the recipient is tailored or customized or otherwise adjusted for the specific needs or specific wants or specific characteristics of the recipient is commonly referred to as fitting.

SUMMARY

In accordance with an exemplary embodiment, there is a method, comprising applying at first and second temporal locations respective electrical currents to an electrode located in a cochlea of a recipient, obtaining first and second data indicative of electrical properties at a plurality of locations away from the electrode, the first and second data corresponding to data obtained, respectively, at the first and second temporal locations, evaluating whether or not there is an existence of a temporal change in electrical conductivity between the electrode and the plurality of locations based on the obtained data, and determining whether or not a phenomenon exists inside the cochlea based on the evaluation.

In another exemplary embodiment, there is a method, comprising applying an electrical current to an electrode located in a cochlea of a recipient, obtaining data indicative of electrical properties at a plurality of locations away from the electrode, evaluating electrical conductivity between plurality of locations based on the obtained data, and determining whether or not a phenomenon exists in the recipient based on spatial derivatives between the locations.

In another embodiment, there is a method, comprising applying an electrical current to an electrode located in a cochlea of a recipient, obtaining data indicative of electrical properties at a plurality of locations away from the electrode, and determining a spatial locational feature of the electrode within the cochlea relative to an anatomical structure of the cochlea based on a gradient of the obtained electrical properties.

In another embodiment, there is a method, comprising applying an electrical current to an electrode located in a cochlea of a recipient, which electrode is a stimulating electrode, obtaining data indicative of respective electrical properties at at least two electrodes located away from the stimulating electrode, obtaining data indicative of an electrical property related to the stimulating electrode, and determining an impedance related feature of the stimulating electrode.

In another exemplary embodiment, there is a method comprising applying electrical current to an intra-cochlea electrode of an implantable medical device, wherein the electrical current is insufficient to evoke a hearing percept in a recipient of the implantable medical device, measuring a voltage induced by the applied electrical current at a plurality of spatially separated intra-cochlea electrodes of the implantable medical device, the measured voltage being indicative of current flowing along a spiral path of the cochlea, and determining a spatial derivative of the measured voltage within the cochlea of the recipient.

BRIEF DESCRIPTION OF THE DRAWINGS

Embodiments are described below with reference to the attached drawings, in which:

FIGS. 3A and 3B are side and perspective views of an electrode assembly extended out of an embodiment of an insertion sheath of the insertion guide illustrated in FIG. 2;

FIGS. 4A-4E are simplified side views depicting the position and orientation of a cochlear implant electrode assembly insertion guide tube relative to the cochlea at each of a series of successive moments during an exemplary implantation of the electrode assembly into the cochlea;

FIGS. 6, 8, 9, 10-14, and 16 present exemplary algorithms for an exemplary methods;

DETAILED DESCRIPTION

Figure 1A:
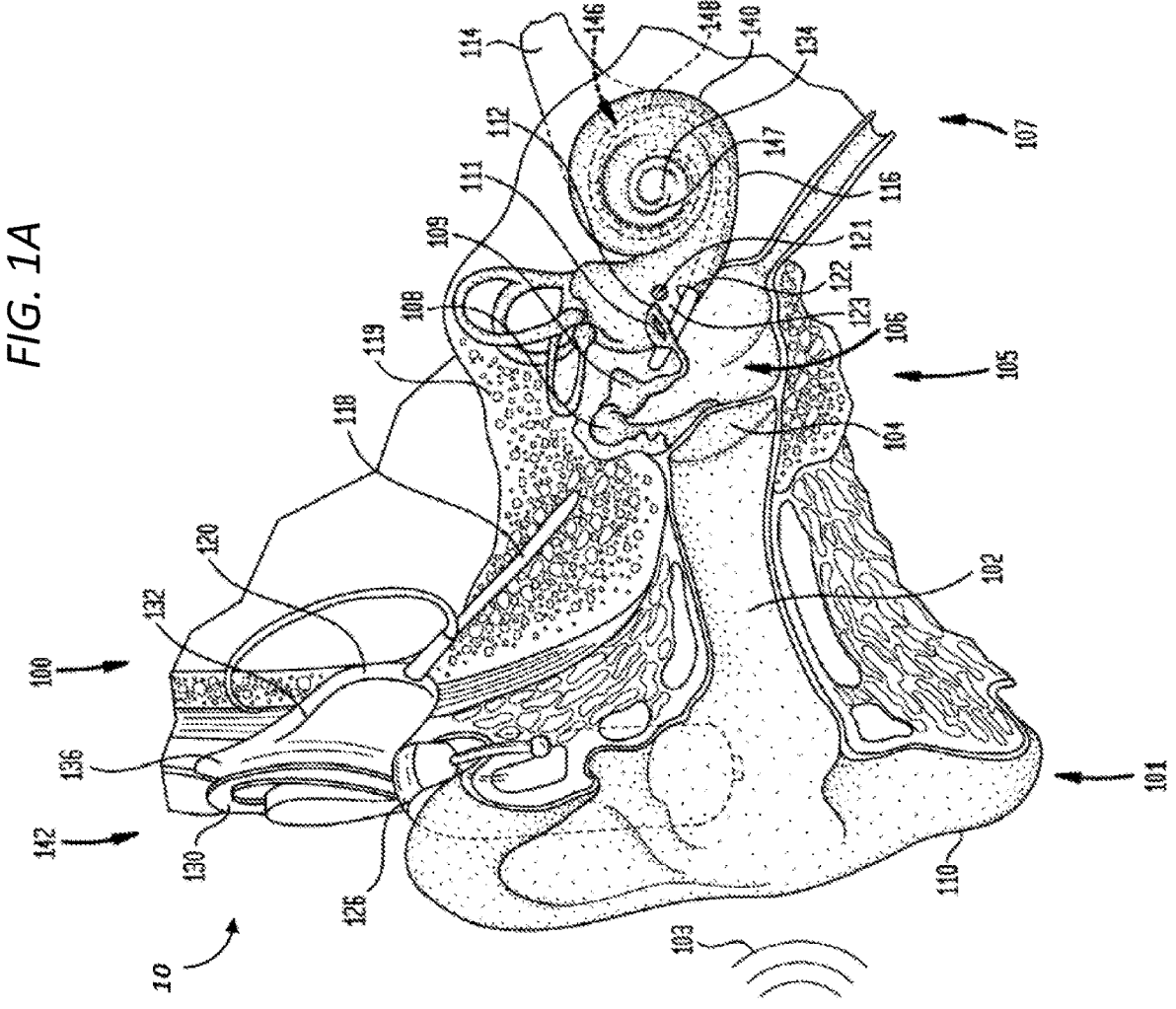
FIG. 1A is a perspective view of an exemplary hearing prosthesis in which at least some of the teachings detailed herein are applicable.

FIG. 1A is a perspective view of a cochlear implant, referred to as cochlear implant 100, implanted in a recipient, to which some embodiments detailed herein and/or variations thereof are applicable. The cochlear implant 100 is part of a system 10 that can include external components in some embodiments, as will be detailed below. Additionally, it is noted that the teachings detailed herein are also applicable to other types of hearing prostheses, such as by way of example only and not by way of limitation, bone conduction devices (percutaneous, active transcutaneous and/or passive transcutaneous), direct acoustic cochlear stimulators, middle ear implants, and conventional hearing aids, etc. Indeed, it is noted that the teachings detailed herein are also applicable to so-called multi-mode devices. In an exemplary embodiment, these multi-mode devices apply both electrical stimulation and acoustic stimulation to the recipient. In an exemplary embodiment, these multi-mode devices evoke a hearing percept via electrical hearing and bone conduction hearing. Accordingly, any disclosure herein with regard to one of these types of hearing prostheses corresponds to a disclosure of another of these types of hearing prostheses or any medical device for that matter, unless otherwise specified, or unless the disclosure thereof is incompatible with a given device based on the current state of technology. Thus, the teachings detailed herein are applicable, in at least some embodiments, to partially implantable and/or totally implantable medical devices that provide a wide range of therapeutic benefits to recipients, patients, or other users, including hearing implants having an implanted microphone, auditory brain stimulators, pacemakers, visual prostheses (e.g., bionic eyes), sensors, drug delivery systems, defibrillators, functional electrical stimulation devices, etc.

In view of the above, it is to be understood that at least some embodiments detailed herein and/or variations thereof are directed towards a body-worn sensory supplement medical device (e.g., the hearing prosthesis of FIG. 1A, which supplements the hearing sense, even in instances when there are no natural hearing capabilities, for example, due to degeneration of previous natural hearing capability or to the lack of any natural hearing capability, for example, from birth). It is noted that at least some exemplary embodiments of some sensory supplement medical devices are directed towards devices such as conventional hearing aids, which supplement the hearing sense in instances where some natural hearing capabilities have been retained, and visual prostheses (both those that are applicable to recipients having some natural vision capabilities and to recipients having no natural vision capabilities). Accordingly, the teachings detailed herein are applicable to any type of sensory supplement medical device to which the teachings detailed herein are enabled for use therein in a utilitarian manner. In this regard, the phrase sensory supplement medical device refers to any device that functions to provide sensation to a recipient irrespective of whether the applicable natural sense is only partially impaired or completely impaired, or indeed never existed.

The recipient has an outer ear 101, a middle ear 105, and an inner ear 107. Components of outer ear 101, middle ear 105, and inner ear 107 are described below, followed by a description of cochlear implant 100.

In a fully functional ear, outer ear 101 comprises an auricle 110 and an ear canal 102. An acoustic pressure or sound wave 103 is collected by auricle 110 and channeled into and through ear canal 102. Disposed across the distal end of ear channel 102 is a tympanic membrane 104 which vibrates in response to sound wave 103. This vibration is coupled to oval window or fenestra ovalis 112 through three bones of middle ear 105, collectively referred to as the ossicles 106 and comprising the malleus 108, the incus 109, and the stapes 111. Bones 108, 109, and 111 of middle ear 105 serve to filter and amplify sound wave 103, causing oval window 112 to articulate, or vibrate in response to vibration of tympanic membrane 104. This vibration sets up waves of fluid motion of the perilymph within cochlea 140. Such fluid motion, in turn, activates tiny hair cells (not shown) inside of cochlea 140. Activation of the hair cells causes appropriate nerve impulses to be generated and transferred through the spiral ganglion cells (not shown) and auditory nerve 114 to the brain (also not shown) where they are perceived as sound.

As shown, cochlear implant 100 comprises one or more components which are temporarily or permanently implanted in the recipient. Cochlear implant 100 is shown in FIG. 1 with an external device 142, that is part of system 10 (along with cochlear implant 100), which, as described below, is configured to provide power to the cochlear implant, where the implanted cochlear implant includes a battery that is rechargeable via the transcutaneous link.

In the illustrative arrangement of FIG. 1A, external device 142 can comprise a power source (not shown) disposed in a Behind-The-Ear (BTE) unit 126. External device 142 also includes components of a transcutaneous energy transfer link, referred to as an external energy transfer assembly. The transcutaneous energy transfer link is used to transfer power and/or data to cochlear implant 100. Various types of energy transfer, such as infrared (IR), electromagnetic, capacitive and inductive transfer, may be used to transfer the power and/or data from external device 142 to cochlear implant 100. In the illustrative embodiments of FIG. 1, the external energy transfer assembly comprises an external coil 130 that forms part of an inductive radio frequency (RF) communication link. External coil 130 is typically a wire antenna coil comprised of multiple turns of electrically insulated single-strand or multi-strand platinum or gold wire. External device 142 also includes a magnet (not shown) positioned within the turns of wire of external coil 130. It should be appreciated that the external device shown in FIG. 1 is merely illustrative, and other external devices may be used with embodiments of the present invention.

Cochlear implant 100 comprises an internal energy transfer assembly 132 which can be positioned in a recess of the temporal bone adjacent auricle 110 of the recipient. As detailed below, internal energy transfer assembly 132 is a component of the transcutaneous energy transfer link and receives power and/or data from external device 142. In the illustrative embodiment, the energy transfer link comprises an inductive RF link, and internal energy transfer assembly 132 comprises a primary internal coil 136. Internal coil 136 is typically a wire antenna coil comprised of multiple turns of electrically insulated single-strand or multi-strand platinum or gold wire.

Cochlear implant 100 further comprises a main implantable component 120 and an elongate electrode assembly 118. In some embodiments, internal energy transfer assembly 132 and main implantable component 120 are hermetically sealed within a biocompatible housing. In some embodiments, main implantable component 120 includes an implantable microphone assembly (not shown) and a sound processing unit (not shown) to convert the sound signals received by the implantable microphone in internal energy transfer assembly 132 to data signals. That said, in some alternative embodiments, the implantable microphone assembly can be located in a separate implantable component (e.g., that has its own housing assembly, etc.) that is in signal communication with the main implantable component 120 (e.g., via leads or the like between the separate implantable component and the main implantable component 120). In at least some embodiments, the teachings detailed herein and/or variations thereof can be utilized with any type of implantable microphone arrangement.

Main implantable component 120 further includes a stimulator unit (also not shown) which generates electrical stimulation signals based on the data signals. The electrical stimulation signals are delivered to the recipient via elongate electrode assembly 118.

Elongate electrode assembly 118 has a proximal end connected to main implantable component 120, and a distal end implanted in cochlea 140. Electrode assembly 118 extends from main implantable component 120 to cochlea 140 through mastoid bone 119. In some embodiments, electrode assembly 118 may be implanted at least in basal region 116, and sometimes further. For example, electrode assembly 118 may extend towards apical end of cochlea 140, referred to as cochlea apex 134. In certain circumstances, electrode assembly 118 may be inserted into cochlea 140 via a cochleostomy 122. In other circumstances, a cochleostomy may be formed through round window 121, oval window 112, the promontory 123 or through an apical turn 147 of cochlea 140.

Electrode assembly 118 comprises a longitudinally aligned and distally extending array 146 of electrodes 148, disposed along a length thereof. As noted, a stimulator unit generates stimulation signals which are applied by electrodes 148 to cochlea 140, thereby stimulating auditory nerve 114.

Figure 1B:
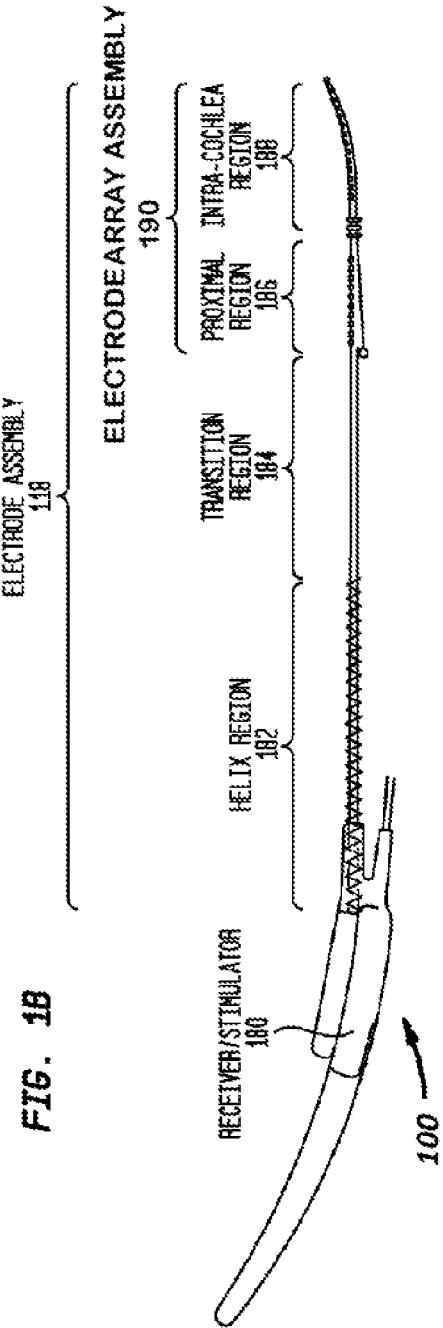
FIG. 1B depicts a side view of the cochlear implant 100 outside of the recipient.

FIG. 1B is a side view of a cochlear implant 100 without the other components of system 10 (e.g., the external components). Cochlear implant 100 comprises a receiver/stimulator 180 and an electrode assembly or lead 118. Electrode assembly 118 includes a helix region 182, a transition region 184, a proximal region 186, and an intra-cochlear region 188. Proximal region 186 and intra-cochlear region 188 form an electrode array assembly 190. In an exemplary embodiment, proximal region 186 is located in the middle-ear cavity of the recipient after implantation of the intra-cochlear region 188 into the cochlea. Thus, proximal region 186 corresponds to a middle-ear cavity sub-section of the electrode array assembly 190. Electrode array assembly 190, and in particular, intra-cochlear region 188 of electrode array assembly 190, supports a plurality of electrode contacts 148. These electrode contacts 148 are each connected to a respective conductive pathway, such as wires, PCB traces, etc. (not shown) which are connected through lead 118 to receiver/stimulator 180, through which respective stimulating electrical signals for each electrode contact 148 travel.

Electrode array 146 may be inserted into cochlea 140 with the use of an insertion guide. It is noted that while the embodiments detailed herein are described in terms of utilizing an insertion guide or other type of tool to guide the array into the cochlea, in some alternate insertion embodiments, a tool is not utilized. Instead, the surgeon utilizes his or her fingertips or the like to insert the electrode array into the cochlea. That said, in some embodiments, alternate types of tools can be utilized other than and/or in addition to insertion guides. By way of example only and not by way of limitation, surgical tweezers like can be utilized. Any device, system, and/or method of inserting the electrode array into the cochlea can be utilized according to at least some exemplary embodiments.

The teachings detailed herein are directed towards identifying phenomenon inside a cochlea. Some embodiments can include utilizing imaging (e.g., CT scan, X-ray, etc.), which require the patient to be exposed to radiation during the process of obtaining medical images, as well as the need for medical equipment in the operating room to provide and otherwise obtain the imaging, as well as a subsequent analysis by an expert to assess the correct insertion of the electrode holder. Some embodiments of the teachings detailed herein utilize such, while other embodiments specifically do not utilize such, but instead utilize other methods to evaluate or otherwise obtain information indicative of a given electrode array insertion scenario. Some embodiments include the action of measuring neuronal activation after stimulation. This exemplary embodiment can require subjective expert analysis and/or can also be dependent on having a good/acceptable neural response. However, in some instances, such is not always obtainable. Again, as with the aforementioned imaging, some embodiments herein utilize such while other embodiments specifically do not utilize such methods. In at least some exemplary embodiments, methods of determining an insertion scenario can utilize voltage measurements in the cochlea. In an exemplary embodiment of such embodiments, the interpretation of the obtained voltage measurements still requires subjective analysis by an expert. In addition, these measurements can be rendered more difficult to interpret than otherwise might be the case by the presence of so-called air bubbles, open electrodes, shorted electrodes, and/or electrode extrusion. Some embodiments of the teachings detailed herein utilize the aforementioned voltage measurements coupled with expert analysis, while in other embodiments some of the teachings detailed herein specifically avoid utilization of expert analysis to obtain or otherwise analyze and electrode array insertion scenario.

Some embodiments include obtaining voltage measurements from inside and/or outside the cochlea and analyzing them in, by way of example only and not by way of limitation, an automated manner, by comparing the voltage measurements to statistical data.

Figure 2A:
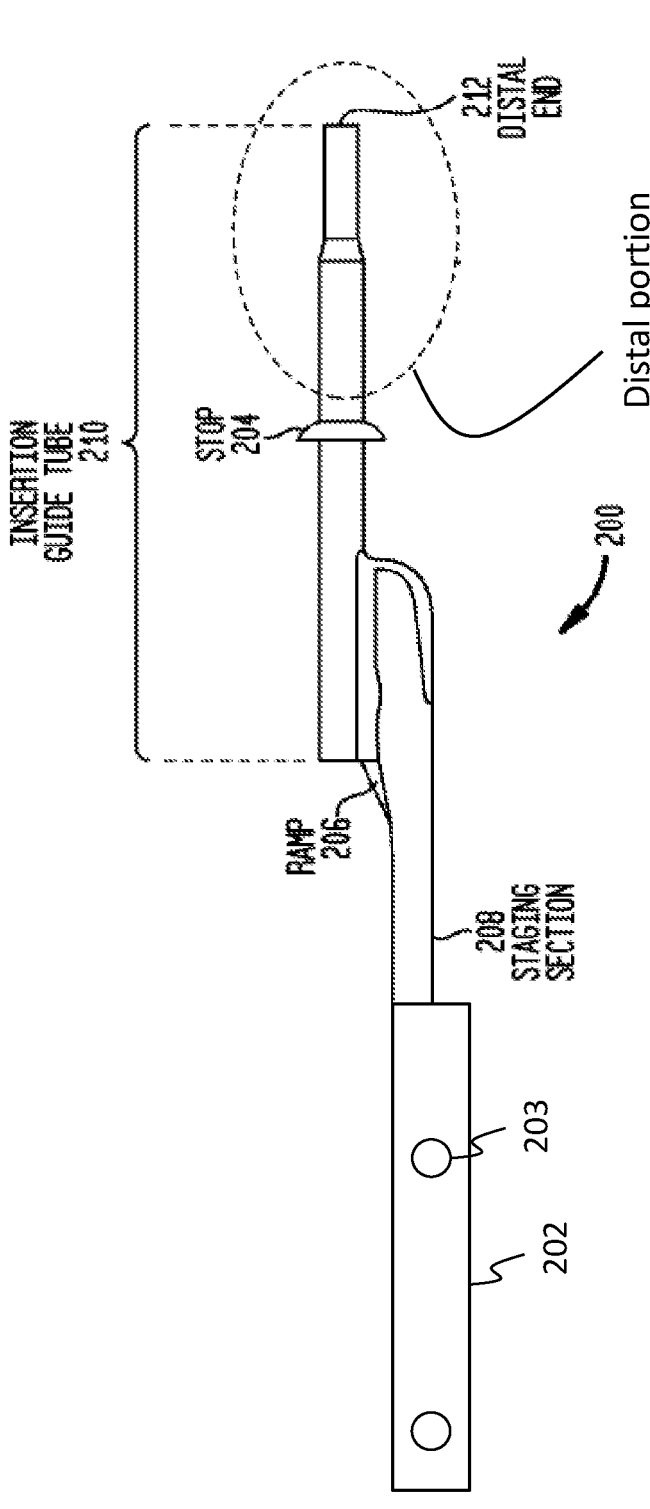
FIGS. 2A and 2B are side views of an embodiment of an insertion guide for implanting a cochlear implant electrode assembly such as the electrode assembly illustrated in FIG. 1.

FIG. 2A presents a side view of an embodiment of an insertion guide for implanting an elongate electrode assembly generally represented by electrode assembly 145 (corresponding to assembly 190 of FIG. 1B) into a mammalian cochlea, represented by cochlea 140. The illustrative insertion guide, referred to herein as insertion guide 200, includes an elongate insertion guide tube 210 configured to be inserted into cochlea 140 and having a distal end 212 from which an electrode assembly is deployed. Insertion guide tube 210 has a radially-extending stop 204 that may be utilized to determine or otherwise control the depth to which insertion guide tube 210 is inserted into cochlea 140.

Insertion guide tube 210 is mounted on a distal region of an elongate staging section 208 on which the electrode assembly is positioned prior to implantation. A robotic arm adapter 202 is mounted to a proximal end of staging section 208 to facilitate attachment of the guide to a robot, which adapter includes through holes 203 through which bolts can be passed so as to bolt the guide 200 to a robotic arm, as will be detailed below. During use, electrode assembly 145 is advanced from staging section 208 to insertion guide tube 210 via ramp 206. After insertion guide tube 210 is inserted to the appropriate depth in cochlea 140, electrode assembly 145 is advanced through the guide tube to exit distal end 212 as described further below.

Figure 2B:
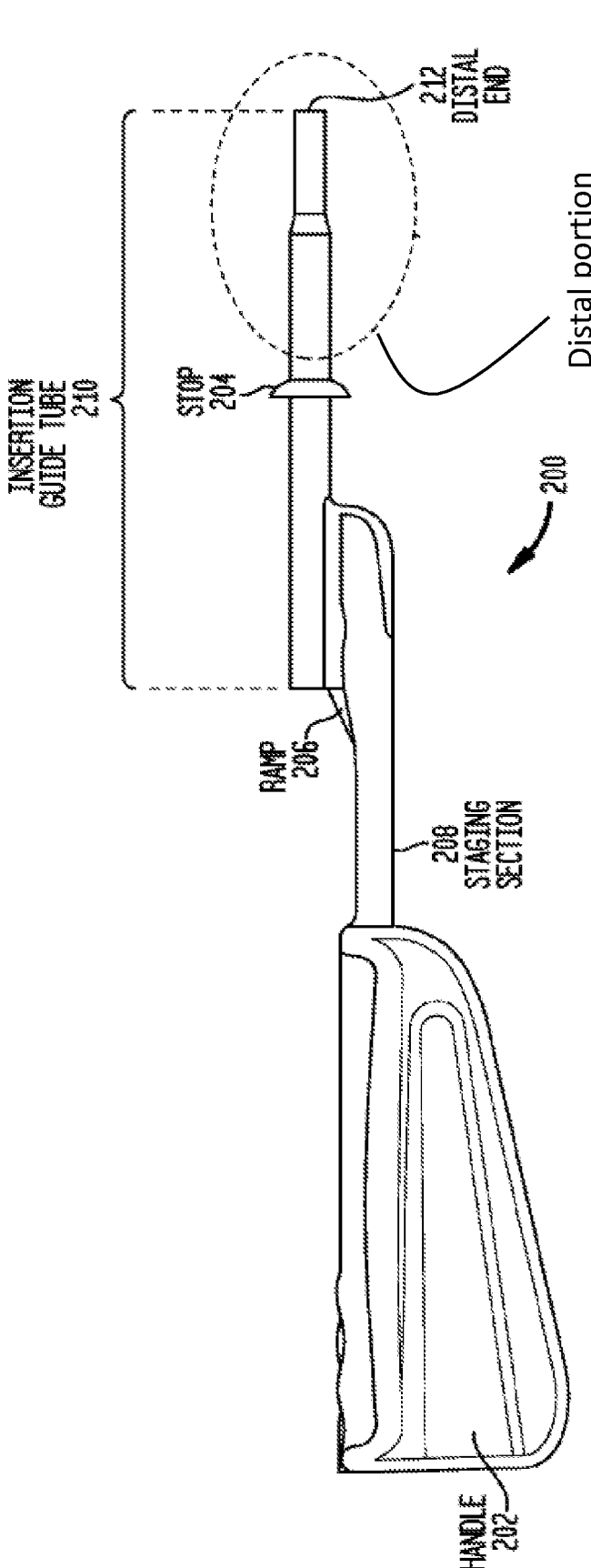

FIG. 2B depicts an alternate embodiment of the insertion guide 200, that includes a handle 202 that is ergonomically designed to be held by a surgeon. This in lieu of the robotic arm adapter 202.

Figure 3A:
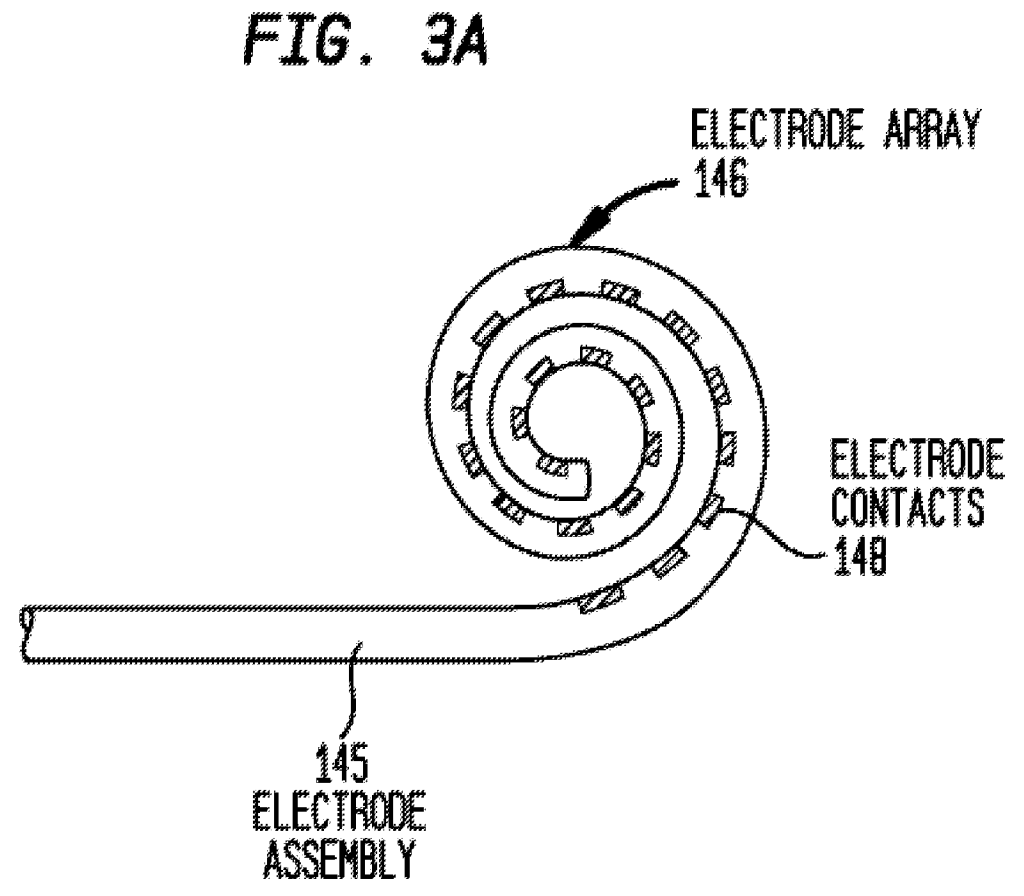
Figure 3B:
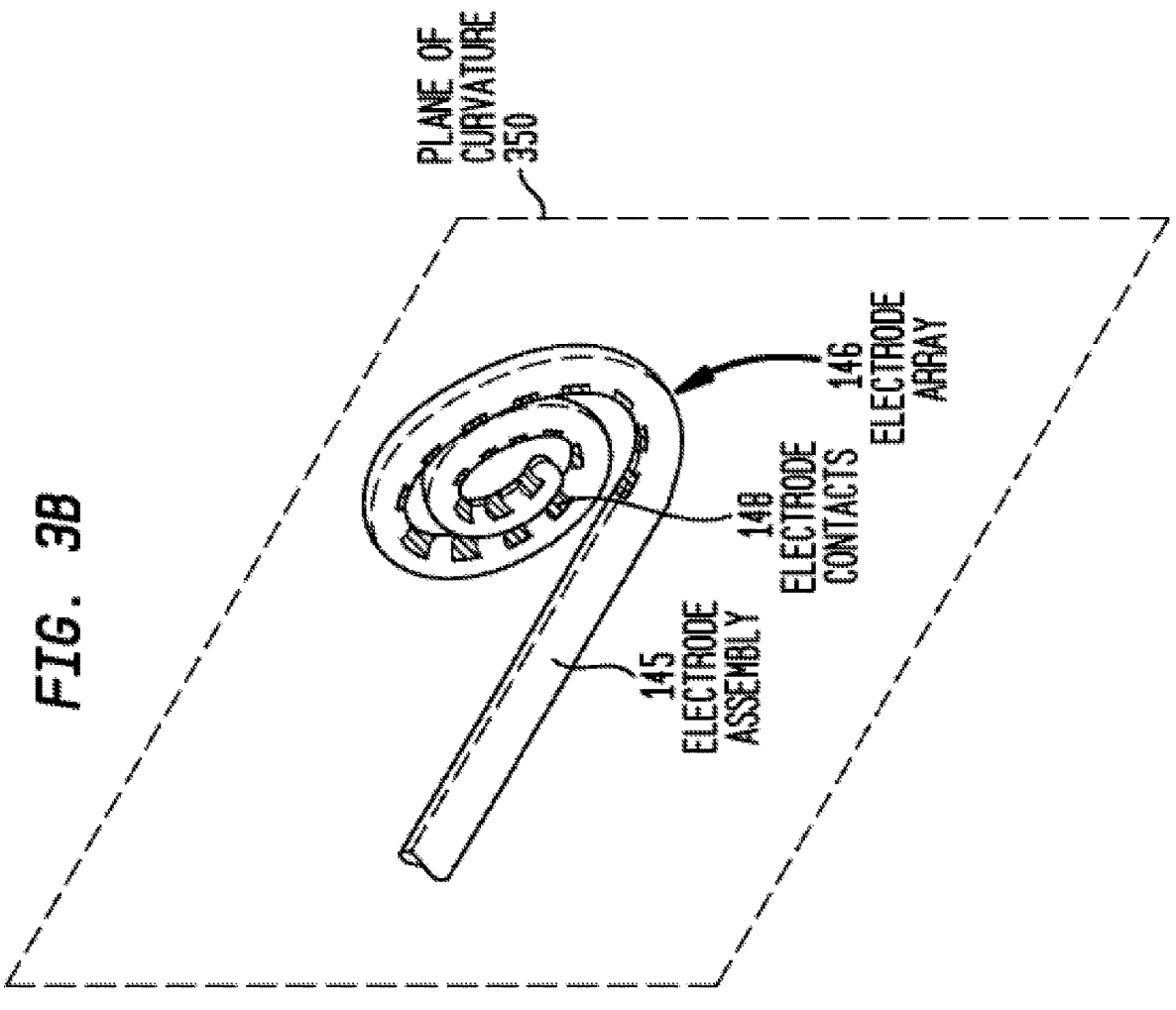

FIGS. 3A and 3B are side and perspective views, respectively, of representative electrode assembly 145. As noted, electrode assembly 145 comprises an electrode array 146 of electrode contacts 148. Electrode assembly 145 is configured to place electrode contacts 148 in close proximity to the ganglion cells in the modiolus. Such an electrode assembly, commonly referred to as a perimodiolar electrode assembly, is manufactured in a curved configuration as depicted in FIGS. 3A and 3B. When free of the restraint of a stylet or insertion guide tube, electrode assembly 145 takes on a curved configuration due to it being manufactured with a bias to curve, so that it is able to conform to the curved interior of cochlea 140. As shown in FIG. 3B, when not in cochlea 140, electrode assembly 145 generally resides in a plane 350 as it returns to its curved configuration. That said, it is noted that embodiments of the insertion guides detailed herein and/or variations thereof can be applicable to a so-called straight electrode array, which electrode array does not curl after being free of a stylet or insertion guide tube, etc., but instead remains straight.

FIGS. 4A-4E are a series of side-views showing consecutive exemplary events that occur in an exemplary implantation of electrode assembly 145 into cochlea 140. Initially, electrode assembly 145 and insertion guide tube 310 are assembled. For example, electrode assembly 145 is inserted (slidingly or otherwise) into a lumen of insertion guide tube 300. The combined arrangement is then inserted to a predetermined depth into cochlea 140, as illustrated in FIG. 4A. Typically, such an introduction to cochlea 140 is achieved via cochleostomy 122 (FIG. 1) or through round window 121 or oval window 112. In the exemplary implantation shown in FIG. 4A, the combined arrangement of electrode assembly 145 and insertion guide tube 300 is inserted to approximately the first turn of cochlea 140.

As shown in FIG. 4A, the combined arrangement of insertion guide tube 300 and electrode assembly 145 is substantially straight. This is due in part to the rigidity of insertion guide tube 300 relative to the bias force applied to the interior wall of the guide tube by pre-curved electrode assembly 145. This prevents insertion guide tube 300 from bending or curving in response to forces applied by electrode assembly 145, thus enabling the electrode assembly to be held straight, as will be detailed below.

As noted, electrode assembly 145 is biased to curl and will do so in the absence of forces applied thereto to maintain the straightness. That is, electrode assembly 145 has a memory that causes it to adopt a curved configuration in the absence of external forces. As a result, when electrode assembly 145 is retained in a straight orientation in guide tube 300, the guide tube prevents the electrode assembly from returning to its pre-curved configuration. This induces stress in electrode assembly 145. Pre-curved electrode assembly 145 will tend to twist in insertion guide tube 300 to reduce the induced stress. In the embodiment configured to be implanted in scala tympani of the cochlea, electrode assembly 145 is pre-curved to have a radius of curvature that approximates the curvature of medial side of the scala tympani of the cochlea. Such embodiments of the electrode assembly are referred to as a perimodiolar electrode assembly, and this position within cochlea 140 is commonly referred to as the perimodiolar position. In some embodiments, placing electrode contacts in the perimodiolar position provides utility with respect to the specificity of electrical stimulation, and can reduce the requisite current levels thereby reducing power consumption.

As shown in FIGS. 4B-4D, electrode assembly 145 may be continually advanced through insertion guide tube 300 while the insertion sheath is maintained in a substantially stationary position. This causes the distal end of electrode assembly 145 to extend from the distal end of insertion guide tube 300. As it does so, the illustrative embodiment of electrode assembly 145 bends or curves to attain a perimodiolar position, as shown in FIGS. 4B-4D, owing to its bias (memory) to curve. Once electrode assembly 145 is located at the desired depth in the scala tympani, insertion guide tube 300 is removed from cochlea 140 while electrode assembly 145 is maintained in a stationary position. This is illustrated in FIG. 4E.

Conventional insertion guide tubes typically have a lumen dimensioned to allow the entire tapered electrode assembly to travel through the guide tube. Because the guide tube is able to receive the relatively larger proximal region of the electrode assembly, there will be a gap between the relatively smaller distal region of the electrode assembly and the guide tube lumen wall. Such a gap allows the distal region of the electrode assembly to curve slightly until the assembly can no longer curve due to the lumen wall.

Returning to FIGS. 3A-3B, perimodiolar electrode assembly 145 is pre-curved in a direction that results in electrode contacts 148 being located on the interior of the curved assembly, as this causes the electrode contacts to face the modiolus when the electrode assembly is implanted in or adjacent to cochlea 140. Insertion guide tube 300 retains electrode assembly 145 in a substantially straight configuration, thereby preventing the assembly from taking on the configuration shown in FIG. 3B.

It is noted that while the embodiments above disclose the utilization of an insertion tool, in some other embodiments, insertion of the electrode array is not executed utilizing an insertion tool. Moreover, in some embodiments, when in insertion tool is utilized, the insertion tool is not as intrusive as that detailed in the figures. In an exemplary embodiment, there is no distal portion of the tool. That is, the insertion tool stops at the location where the distal portion begins. In an exemplary embodiment, the tool stops at stop 204. In this regard, there is little to no intrusion of the tool into the cochlea. Any device, system and/or method that can enable the insertion of the electrode array can be utilized in at least some exemplary embodiments.

It is also noted that while the above embodiments have been described in terms of insertion/a method of inserting the electrode, the teachings detailed herein are also applicable to post insertion methods, as will be described below.

Figure 22:
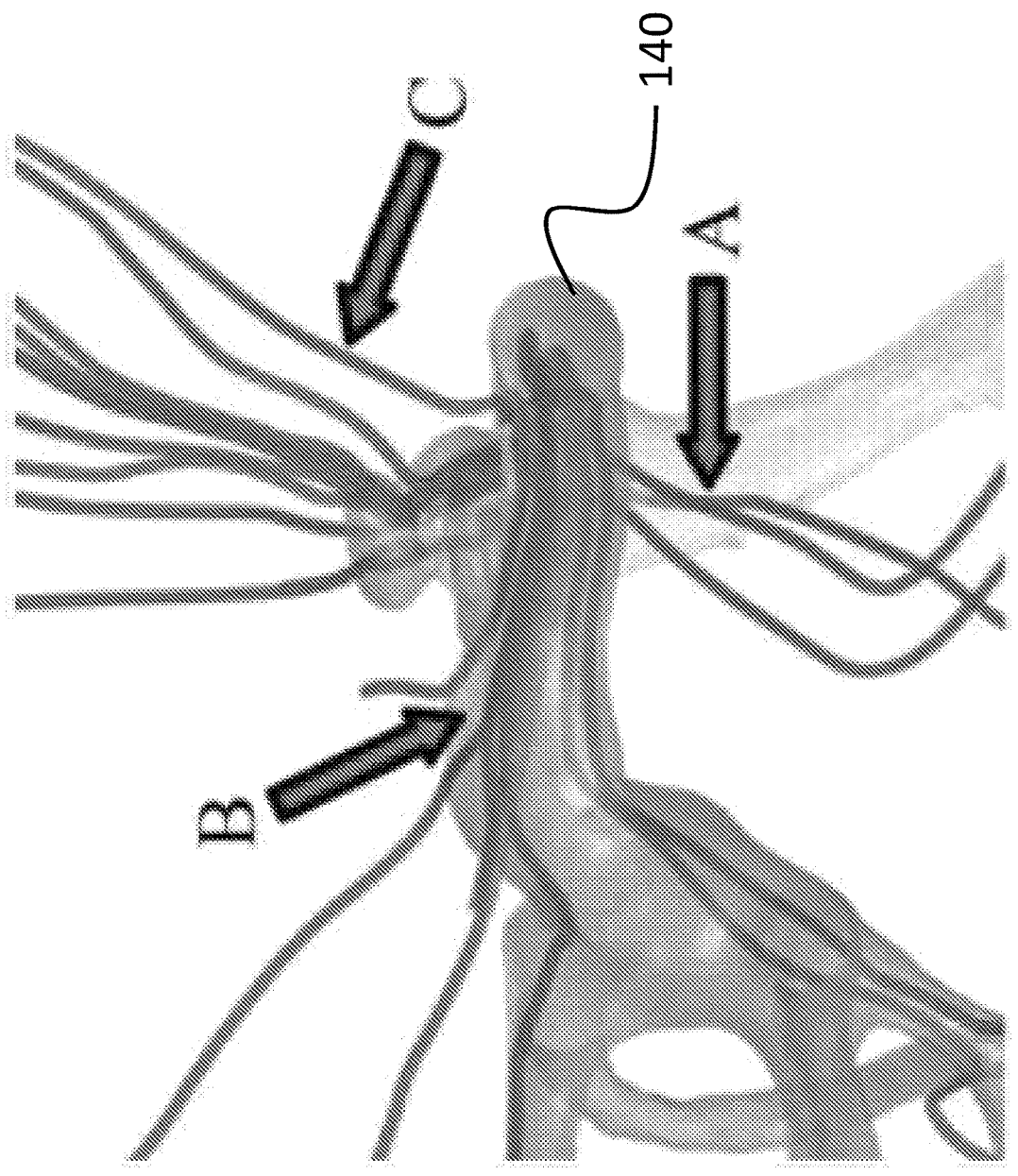
FIGS. 22 and 23 depict exemplary current flow in a recipient of a cochlear implant.
Figure 23:
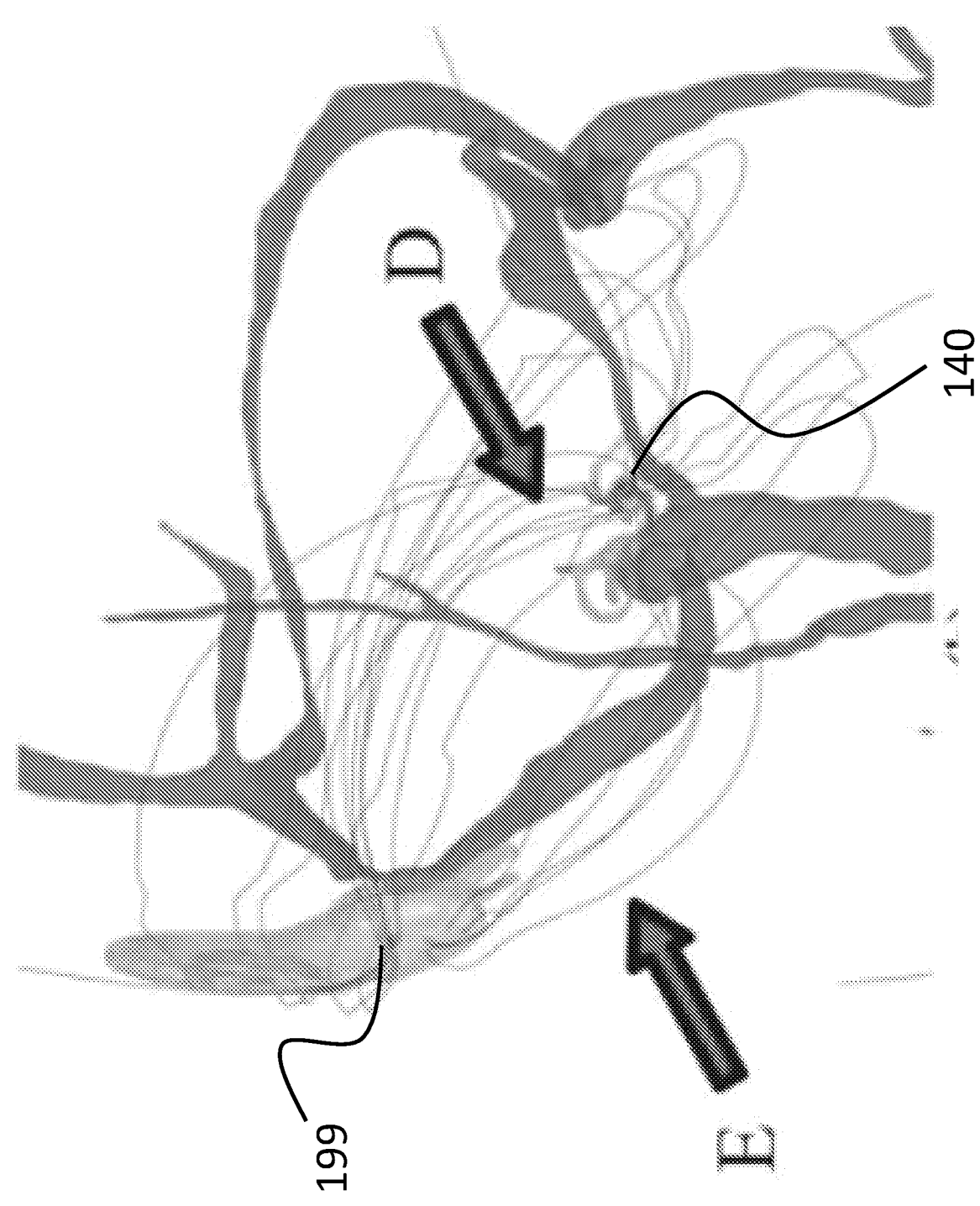

Exemplary teachings detailed herein utilize at least one electrode of the electrode array as a stimulating electrode and utilizing at least one electrode implanted in the recipient as a read electrode to obtain data relating to a situation that exists in the recipient. In some instances, without being bound by theory, current flows from an intracochlear to an extracochlear electrode during monopolar stimulation of an electrode array that is inserted into the cochlea (partially and/or fully), the current can follow one or more or several paths. In some embodiments, again without being bound by theory, within the cochlea, referring to FIGS. 22 and 23, there are three major paths of current in and around the cochlea—current through the cochlea traveling along the spiral (Path B in FIG. 22—path parallel to cochlear spiral), current flowing along a path generally parallel to the axis of rotation of the spiral (e.g., within a cone of about 30 degrees or so centered on the axis), which path is below the spiral (Path A in FIG. 22—path through auditory nerve that causes percept of sound), and current flowing along a path generally parallel to the axis of rotation of the spiral (gain, within a cone of about 30 degrees or so centered on the axis), which path is above the spiral (Path C in FIG. 22—path through walls of cochlea), and once outside the cochlea, in some instances, current, mostly flows via the brain (Path D in FIG. 23) and scalp (Path E in FIG. 23), to the extracochlear electrode (199 in FIG. 23, which is on the receiver-stimulator) of a cochlear implant.

Figure 5:
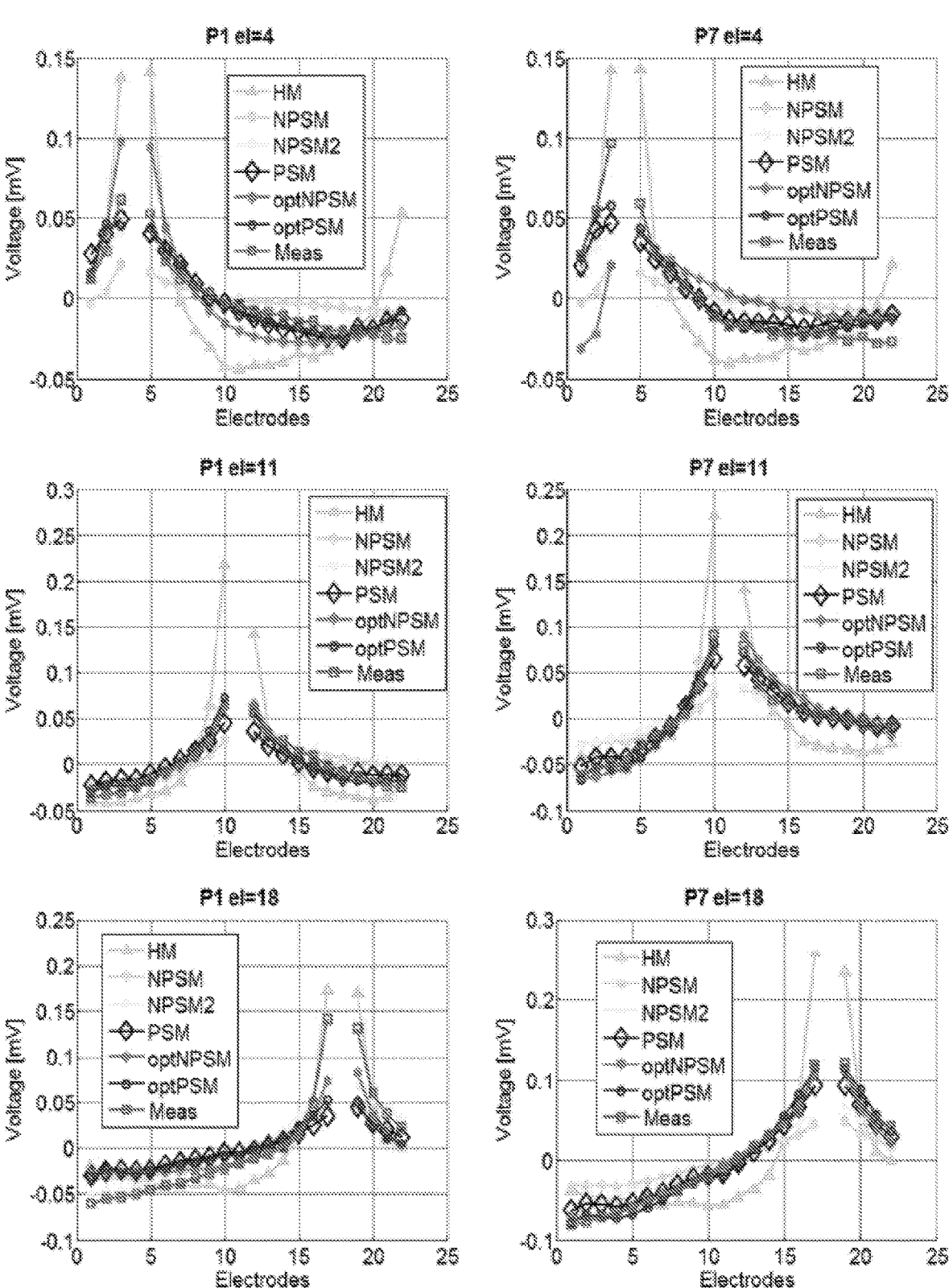
FIGS. 5 and 7 presents exemplary data according to an exemplary embodiment.

Voltage measurements can be made at one or more or all of the contacts (electrodes) of the electrode array while the above noted current is flowing. Examples of these voltage measurements are show in FIG. 5. The various curves are for different regimes of measurement/prediction. In an exemplary embodiment, providing that a consistent regime of measurement or prediction is utilized, any regime of measurement that can enable the teachings detailed herein or variations thereof can be utilized in at least some exemplary embodiments. More specifically, the curves marked "Meas" are measured values from the recipients. Other curves are the predicted voltages using various models of the cochlea using various techniques identified. FIG. 5 shows examples of voltage measurements (y axis) made at 22 electrodes (x axis) during monopolar stimulation. Values shown are from two recipients—P1 (left column) and P7 (right column). Stimulation is at three different electrodes—4 (top row), 11 (middle row) and 18 (bottom row). The voltage measurements shown in FIG. 3 take on the general form of a "skirt" centered on the stimulating electrode. Embodiments utilize these skirts to execute diagnostic and data-gathering methods, results of which can be utilized to infer otherwise deduce occurrences of features in the cochlea.

FIG. 6 depicts an exemplary flowchart for an exemplary method, method 600, which includes method action 610, which includes the action of applying at first and second temporal locations respective electrical currents to an electrode located in a cochlea of a recipient. Method 600 also includes method action 620, which includes obtaining first and second data indicative of electrical properties at a plurality of locations away from the electrode, the first and second data corresponding to data obtained, respectively, at the first and second temporal locations. By way of example only and not by way of limitation, method action 610 can correspond to providing electrical stimulation at electrode 11 (known current and/or voltage applied to electrode 11, for example), and method action 620 can correspond to reading the voltages and/or currents at electrodes 12, 13, 14, 15, 10, 9, 8, 7, and/or 6, etc. This is done at a first temporal location, such as at time zero, and then is repeated at a second temporal location, such as at time 1 month (more on this below). It is noted that in an exemplary embodiment, the data obtained can be obtained at all of the other electrodes. In this exemplary embodiment, the extra cochlear electrode is also a stimulating electrode and that it is utilized alternately as a source and sink, along with the stimulating electrode of the cochlear electrode array (electrode 11 in this instance). In an exemplary embodiment, the obtained data can correspond to, for example, the data, that, when charted according to the plots of FIG. 5, the data shown in FIG. 5.

It is noted that by reciting "applying at first and second temporal locations respective electrical currents to an electrode," this need not necessarily be the same electrode. That is, this action includes both the application of electrical current to the same electrode at the two temporal locations and the application of a current to another electrode different than that applied to the electrode during the first temporal location. That said, in some other embodiments, the electrode is the same. This is also the case with respect to method action 620. The electrodes that are utilized as the read electrodes need not necessarily be the same at the first and temporal locations although in other embodiments, the electrodes are the same at the first and temporal locations. Any arrangement of utilization of electrodes that can enable the teachings detailed herein can be utilized in at least some exemplary embodiments.

Method 600 further includes method action 630, which includes evaluating whether or not there is an existence of a temporal change in electrical conductivity between the electrode and the plurality of locations based on the obtained data. In an exemplary embodiment, this is done by comparing the data obtained at the first temporal location with the data obtained at the second temporal location. Method 600 also includes method action 640, which includes the action of determining whether or not a phenomenon exists inside the cochlea based on the evaluation. In an exemplary embodiment, this phenomenon can be a phenomenon indicative of damage in the cochlea. Some additional details of this will be described in greater detail below.

It is noted that in some exemplary embodiments, the current applied by the implanted device is such that the current is applied at a sub threshold level. In an exemplary embodiment, no hearing percept is evoked when the current is applied. In some embodiments, a relatively minor hearing pursuit may be evoked, but one that is generally not noticeable or otherwise not distracting to the recipient. In an exemplary embodiment, the temporal nature or otherwise frequency of the current applications is such that to the extent a hearing percept is in theory evoked, it is not noticed by the recipient.

In an exemplary embodiment, the temporal change in electrical conductivity is a change in the spatial derivative of voltage between the electrode and the locations. In an exemplary embodiment, the temporal change in electrical conductivity is a change in the spatial derivative of voltage between locations. In an exemplary embodiment, the temporal change in electrical conductivity is not a change in the spatial derivative of voltage between the electrode and the locations, but instead a change in the spatial derivative of voltage between locations. In this regard, in an exemplary embodiment, with reference to FIG. 5, it can be seen that the slope of the line between the locations is plotted in the figures. This can be considered the spatial derivative between the locations (note that the spatial derivative between the location of the electrode is not shown—this is because, in some embodiments, one cannot utilize the stimulating electrode is a read electrode—more on this below). The slope of the line between the locations can change between the temporal locations. This can correspond to a change in the spatial derivative between the locations. In an exemplary embodiment, this change can indicate the occurrence of a phenomenon in the recipient relative to that which was the case at the time zero.

While the embodiment just described focuses on the derivative of voltage, it is to be understood that other electrical phenomena can be utilized. Any electrical phenomenon that can be measured, inferred, or otherwise estimated that can enable a temporal change in a spatial derivative thereof to be determined can be utilized in at least some exemplary embodiments.

It is noted that while the embodiment just described requires only a detection of a change in the spatial derivative, in an exemplary embodiment, the magnitude of the change in the spatial derivative and/or the direction of change in the spatial derivative is utilized to deduce or otherwise infer or otherwise determine whether or not a phenomenon exists inside the cochlea based on the evaluation. Any device, system, and/or method of evaluating the change in the spatial derivative of the electrical property can be utilized in at least some exemplary embodiments.

In an exemplary embodiment, the temporal change in electrical conductivity is due to a change in resistivity of the material. In an exemplary embodiment, the temporal change in electrical connectivity is due to a change in the resistivity of the perilymph in the cochlea. More specifically, in some embodiments, the values of impedance between locations (electrodes) are proportional to the resistivity of perilymph and/or any other material in the cochlear scalae. Therefore, if an electrode array is stationary in the scalae (and at least some of the methods herein are executed for stationary locations over the temporal periods, at least relative to structure of the cochlea), in some embodiments, a change in the spatial derivative of voltage is due to a change in the resistivity of perilymph and/or other material within the scalae. The teachings herein use this change to identify the occurrence of, for example, an infection and/or mechanical trauma within the cochlea (which potentially causes changes in resistivity, and thus the detected/determined change in the derivative). Accordingly, the spatial derivative of voltage is used, in some embodiments, as a marker of infection and/or other damage mechanisms in the cochlea.

Figure 7:
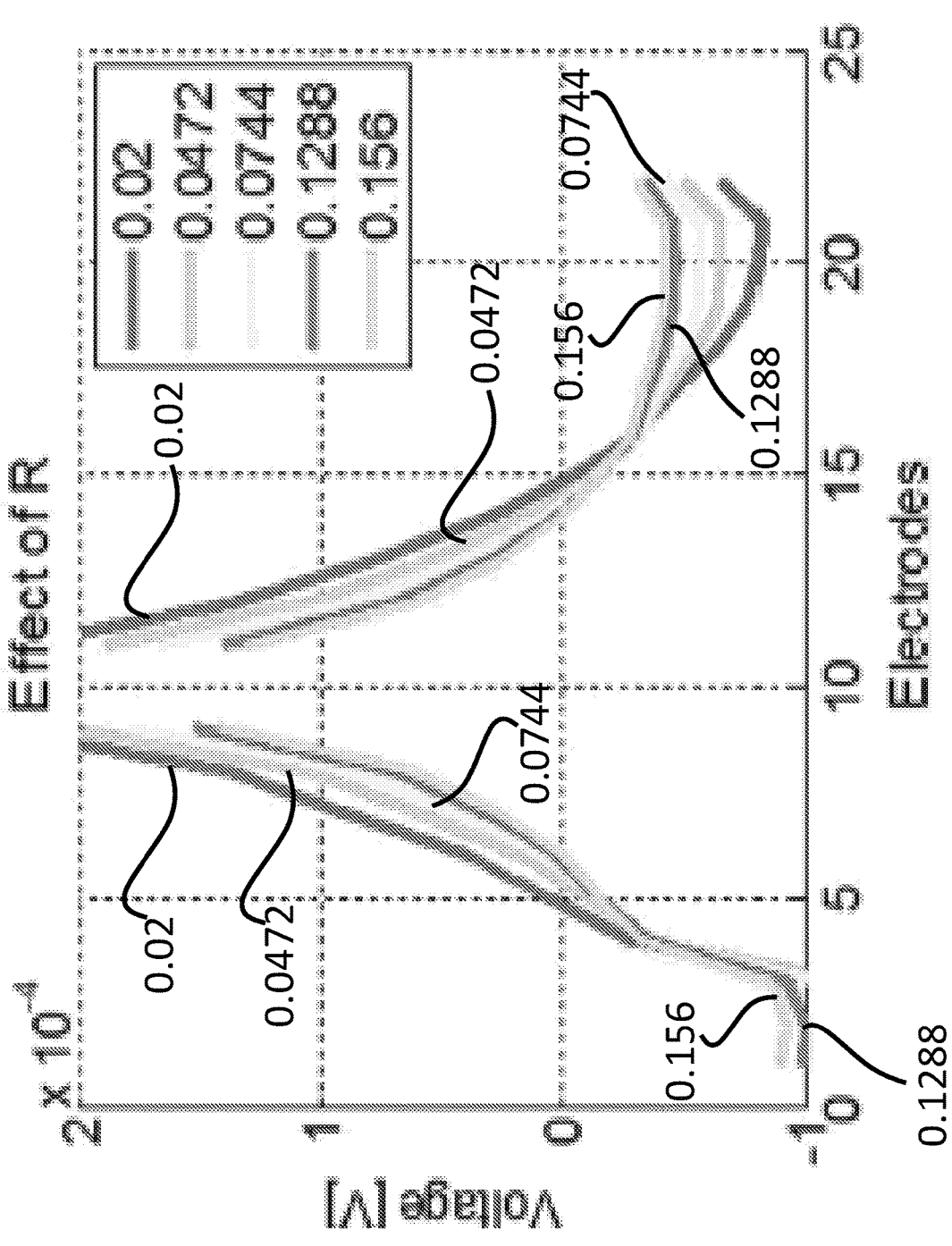

FIG. 7. shows exemplary voltage gradients between locations of read electrodes in the scalae for different values of the perilymph resistivity (high R is high perilymph resistivity) ball measured based on the utilization of electrode 10 as the stimulating electrode, the other electrodes being the read electrodes. As can be seen, the spatial derivative of the voltage measurements at the read electrodes changes for different changes in resistivity.

As noted above, in some embodiments, the difference in time zero and the second temporal period is one month. In some embodiments it is more and in some embodiments it is less. The time period over which resistivity changes occur can be utilized as a marker to interpret any changes/identify the occurrence of phenomenon. In at least some exemplary embodiments, changes in resistivity due to cochlear damage would occur in hours or days so if the resistivity variation occurred over this timescale, this could lead to a determination of a damage related occurrence within the cochlea. That is, the resistivity variation on the aforementioned timescales can be evidence of a damage related mechanism. By identifying the change within those timescales, the determination can be made that a damage related event has occurred. Such can have utilitarian value in at least some exemplary embodiments where real time awareness of any injury within the cochlea may be useful in preventing loss of residual hearing. Some exemplary embodiments entail identifying that damages occurring (early enough, by, for example, repeatedly reading the read electrodes and evaluating whether or not a change in the spatial derivative has taken place) If damage is occurring, the recipient can be given a course of drugs, such as corticosteroids, for example, which can be protective of residual hearing.

Figure 8:
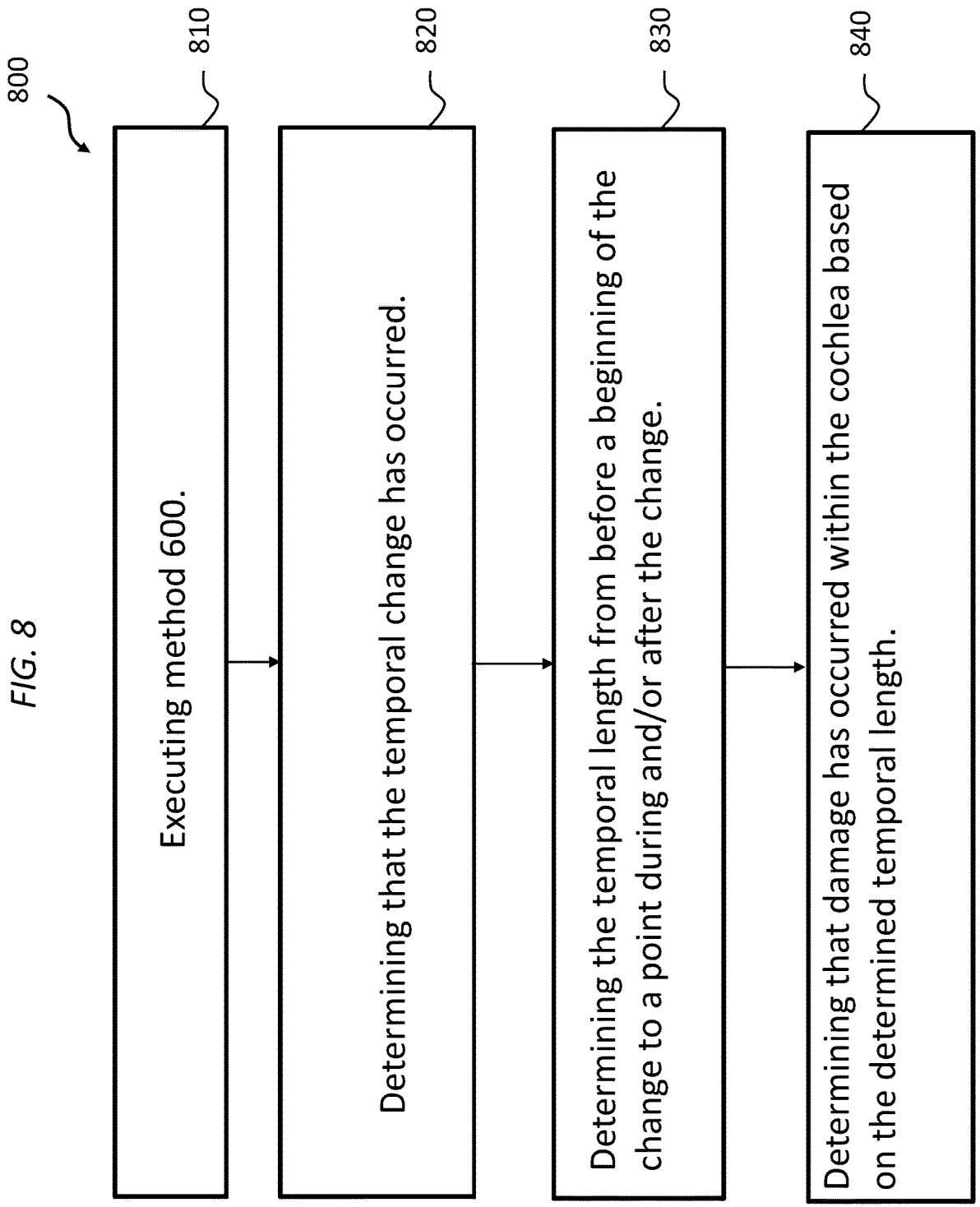

Accordingly, in an exemplary embodiment, there is a method 800 according to the algorithm seen in FIG. 8. Method 800 includes method action 810, which includes executing method 600. Method 800 also includes method action 820, which includes determining that the temporal change has occurred (as opposed to a scenario associated with method action 630 where one determines that the temporal change has not occurred). Method action 820 can be executed manually and/or automatically. Method action 820 can be executed utilizing any data manipulation/evaluation algorithm that can determine that the temporal change has occurred. Method 800 also includes method action 830, which includes determining the temporal length from before a beginning of the change to a point during and/or after the change. In an exemplary embodiment, the temporal length from before a beginning of the change can be a time from the final positioning of the electrode array during an electrode array insertion surgery to a second time after that where the change has begun to occur or has completely occurred. This can be the time between the first temporal location and the second temporal location of method 600.

In an exemplary embodiment, the first temporal location can be the time at which the cochlear implant electrode array is fully positioned in the cochlea and no further adjustments to his locations are made. In an exemplary embodiment, the first temporal location could be a time at which the incision into the recipient to access the cochlea is fully closed (e.g., the last suture and/or stitch or whatever is applied). In an exemplary embodiment, the first temporal location could be a time at which the electrode array is fixed to the recipient. In an exemplary embodiment, the first temporal location could be a time beginning at an arbitrary time after the completion of the surgery implanting the array into the recipient (e.g., midnight, 6 am, etc.). In an exemplary embodiment, the first temporal location exists at about/on the order of X hours or about/on the order of X days or about/on the order of X weeks or about/on the order of X months after any of the aforementioned occurrences, where X is 0.1, 0.2, 0.3, 0.4, 0.5, 0.6, 0.7, 0.8, 0.9, 1.0, 1.25, 1.5, 1.75, 2.0, 2.25, 2.5, 2.75, 3.0, 3.5, 4, 4.5, 5, 5.5, 6, 6.5, 7, 7.5, 8, 9.5, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 110, 120, 130, 140, 150, 160, 170, 180, 190, 200, 225 or 250 or any value or range of values therebetween in 0.01 increments (e.g., 0.23, 45.07, 0.33 to 83.3, etc.). In an exemplary embodiment, the first temporal location can be any temporal location that can have utilitarian value. By way of example only and not by way of limitation, because the teachings detailed herein are novel, the teachings detailed herein can be utilized in existing cochlear implants already implanted in a recipient. In an exemplary embodiment, a recipient could go in to see a doctor or the like having sufficient equipment so as to operate the cochlear implant so as to execute method 600, where method action 600 was never executed utilizing that cochlear implant, even though the cochlear implant have been implanted months and/or years before. That time, that first utilization of the cochlear implant to execute method 600 can be the first temporal location.

In an exemplary embodiment, the second temporal location exists at about X hours or about/on the order of X days or about/on the order of X weeks or about/on the order of X months after the first temporal location.

Returning back to method 800, in an exemplary embodiment, there is method action 840, which includes determining that damage has occurred within the cochlea based on the determined temporal length. In an exemplary embodiment, this is the time between temporal location 1 and temporal location 2, which can thus equal any of/about/on the order of X hours, X days or X weeks or X months.

In an exemplary embodiment, upon a determination that the temporal length in method action 830 is, for example, 2.75 hours, a determination can be made that damage has occurred in the cochlea. This is compared to, for example, a length of time corresponding to, for example, 80 months or so, where the occurrence of a change could be indicative of more general phenomenon associated with damage (e.g., normal growth of the recipient).

Thus, as can be seen, in an exemplary embodiment, the method can include determining the order of the temporal length from before the beginning of the change to the point during and/or after the change, where the time can be on the order of 2, 3, 4, 5, 6, 7, 8, 9, or 10 hours or any value between 2 and 10 hours. In an exemplary embodiment, the method also includes determining that damage or infection (the two are not mutually exclusive) has occurred within the cochlea based on the determined temporal length being on the order of 2, 3, 4, 5, 6, 7, 8, 9 or 10 hours or any value between 2 and 10 hours. In an alternative embodiment, the method includes determining that temporal length is on the order of values that are greater than the aforementioned values/any of the values of X hours, days, weeks, or months, and determining the damage or infection has not occurred based on such. Further, as can be seen, in an exemplary embodiment, the method can include determining the order of the temporal length from before the beginning of the change to the point during and/or after the change, where the time can be on the order of $\frac{1}{4}^{th}$, $\frac{1}{2}$th, $\frac{3}{4}$th, 1, 1 and $\frac{1}{4}^{th}$, 1 and $\frac{1}{2}$th, 1 and $\frac{3}{4}^{th}$, 2, 2 and $\frac{1}{4}^{th}$, 2 and $\frac{1}{2}$th, 2 and $\frac{3}{4}^{th}$, or 3 days or any value between $\frac{1}{4}^{th}$ and 3 days. The method can include determining that damage or infection has occurred within the cochlea based on the determined temporal length being on the order of $\frac{1}{4}^{th}$, $\frac{1}{2}$th, $\frac{3}{4}$th, 1, 1 and $\frac{1}{4}^{th}$, 1 and $\frac{1}{2}$th, 1 and $\frac{3}{4}^{th}$, 2, 2 and $\frac{1}{4}^{th}$, 2 and $\frac{1}{2}$th, 2 and $\frac{3}{4}^{th}$, or 3 days or any value between $\frac{1}{4}$th and 3 days. In an alternative embodiment, the method includes determining that temporal length is on the order of values that are greater than the aforementioned values/any of the values of X hours, days, weeks, or months, and determining the damage or infection has not occurred based on such.

In an exemplary embodiment, there is a method that includes the action of determining that the temporal length from before the beginning of the change to the point during and/or after the change is on the order of 5, 10, 15, 20, 25, 30, 35, 40, 45, 50, 55, 60, 65, 70, 75, 80, 85 or 90 days or any values between 5 and 90 days. That method further includes the action of determining that damage or infection has occurred within the cochlea based on the determined temporal length being on the order of 5, 10, 15, 20, 25, 30, 35, 40, 45, 50, 55, 60, 65, 70, 75, 80, 85, or 90 days or any values between 5 and 90 days. In an alternative embodiment, the method includes determining that temporal length is on the order of values that are greater than the aforementioned values/any of the values of X hours, days, weeks, or months, and determining the damage or infection has not occurred based on such.

It is noted that in at least some exemplary embodiments, the actions of applying the electrical currents to the electrode and the actions of obtaining the first and second data, and the actions of evaluating whether or not there exists a temporal change, and/or determining whether or not the phenomenon exists inside the cochlea can be repeatedly executed during any of the aforementioned time periods. In an exemplary embodiment, method 600 can be executed 10, 20, 30, 40, 50, 60, 70, 80, 90, 100, 125, 150, 200, 300 or more times after implantation of a cochlear electrode array. In an exemplary embodiment, this can result in a data set of values from the read electrodes for multiple temporal locations. Indeed, data from the read electrodes can be present for 10, 20, 30, 40, 50, 60, 70, 80, 90, 100, 125, 150, 200, 300 temporal locations. Indeed, in an exemplary embodiment, method 600 can be executed 1, 2, 3, 4, 5, 6, 7, 8, 9, 10, 15, 20, 30, 40, 50, 60, 70, 80, 90, 100, 125, 150, 200, 300, or more or any value or range of values therebetween in one increment times per day, per week, per month, etc. In an exemplary embodiment, via the implant or a remote device or by manual operation, the data can be recorded and catalogued based on temporal location. In some embodiments, every time a new data set is obtained, the data set can be compared to the temporally adjacent most prior set of data, and were to data sets prior thereto. Comparisons can be made between the data sets, and if a change is detected, based on the temporal length between the two data sets, a determination can be made as to what type of damage has occurred or whether or not damage has occurred in the first instance.

It is also noted that in at least some exemplary embodiments, a plurality of electrodes are utilized as the stimulating electrodes, and other electrodes are utilized as the read electrodes. In an exemplary embodiment, each of the aforementioned executions of method 600 is executed for every electrode as the stimulating electrode. That is, in an exemplary embodiment, electrode one is utilized as the stimulating electrode, and the remaining 21 electrodes are utilized as the read electrodes, then electrode two is utilized as the stimulating electrode, and the remaining 21 electrodes are utilized as the read electrodes, and so on. The aforementioned first location can correspond to the time from the beginning of the energizing of electrode 1, through all of the electrodes up to the electrode 22, and after the read electrodes are utilized to read the voltages when the lecture 22 is energized, that can be the end of the first temporal location. As can be seen, a matrix of data can be developed for the first temporal location. This process can be repeated at the second temporal location, and the data sets of the two matrices can be compared. In some embodiments, not all electrodes are stimulated. Indeed, in some embodiments, the most apical and most distal electrodes are not utilized as stimulating electrodes, owing to the fact that in at least some exemplary embodiments, a voltage gradient cannot be developed for electrodes on both sides of that stimulating electrode, because there are none.

In an exemplary embodiment, upon a determination that the temporal change has occurred, the method includes providing the recipient with drugs based solely on the determination.

In an exemplary embodiment, the data indicative of electrical properties for the locations of the plurality of locations can be plotted to obtain respective curves, such as those seen in the figures by way of example. A method action can be executed that entails determining whether or not a change of a slope and one or more of the respective curves has occurred to determine whether or not the aforementioned phenomenon exists. In an exemplary embodiment, this can be done by sight. In an exemplary embodiment, this can be done by video enhancement showing the change in the slope. In an exemplary embodiment, a method action can be executed that entails determining whether or not a curve has moved as opposed to simply determining whether or not a change in slope has occurred.

In any event, it is to be noted that in at least some exemplary embodiments, there can be utilitarian value with respect to considering multiple locations for the first derivative changes. By way of example only and not by way of limitation, such as by reference to FIG. 7, it can be seen that the slopes of the curves for the resistivity of perilymph equal to 0.02 and for the resistivity of perilymph equal to 0.0472 appear to be about the same between the electrodes closest to the stimulating electrode (electrode 10). However, when the change in the voltages is considered over the entire curves, it can be seen that the slope changes much more prominently. Accordingly, in an exemplary embodiment, the action of determining the differential between the locations includes determining an average differential for multiple locations, and comparing that average to the average at the prior temporal location. It is noted that any statistical averaging can be utilized, whether such is mean, median, and/or mode. Still further, so as to address changes from positive to negative derivatives, in an exemplary embodiment, a least mean squares can be utilized. Any arrangement or any method or any number of locations that can be utilized as read electrodes that can enable the teachings detailed herein can be utilized in at least some exemplary embodiments.

Some exemplary embodiments of the teachings detailed herein can be utilized to identify the occurrence of growth of fibrous tissue. By way of example only and not by way of limitation, growth of fibrous tissue in the cochlea can, in some instances, result in increase in resistivity of the material in the scalae. In the case of fibrous tissue, the increase in resistivity will typically occur over weeks or months. So if the resistivity increases, e.g., steadily, over that time period, the change can be considered an indicator of the amount of fibrous tissue present in the cochlea. Knowledge of the extent of fibrous tissue in the cochlea (which does not show up on x-ray) assists, in some embodiments, surgeons in planning and/or determining whether or not a revision surgery is utilitarian or otherwise could be needed. In some exemplary embodiments, if it is known that fibrous tissue in the cochlea is increasing, such as by evaluating the spatial differential changes, etc., actions can be taken to halt or reverse or slow its growth by, for example, administering drugs such as corticosteroids. In an exemplary embodiment, by limiting or otherwise reducing or otherwise eliminating or otherwise preventing fibrous tissue build-up, the increased impedances associated with this phenomenon and the resulting higher power drain for of the cochlear implant (or, more specifically, the external component that is powering the implanted component) can be mitigated if not avoided entirely.

Accordingly, in an exemplary embodiment of executing method 600, there can be an additional action of determining that the temporal change has occurred, consistent with method action 820 detailed above. The method can also include the action of executing a revision surgery based at least in part on the determination that the temporal changed has occurred. In this exemplary method, fibrous tissue has built up proximate the electrode and/or one or more of the locations, which fibrous tissue has cause the temporal change, and which fibrous tissue is transparent to x-rays.

Thus, there is, in some exemplary embodiments, the action of determining that the temporal change has occurred, which change has occurred steadily over a period of week(s) and/or months. In an exemplary embodiment, based on this determination, a determination is made that fibrous tissue has built up proximate the electrode and/or one or more of the locations based on the determination, which fibrous tissue has caused the temporal change, and which fibrous tissue is transparent to x-rays, wherein fibrous tissue has built up (and thus this is not a false positive). In an exemplary embodiment, there is also the action of determining an amount of the fibrous build up based on the temporal change, wherein fibrous tissue has built up in at least about the amount determined.

It is noted that in at least some exemplary embodiments, when a damage scenario has occurred, there can be an influx of white blood cells or other immune system cells into the cochlea. This can occur, for example, as a result of trauma, such as insertion trauma when the electrode array is inserted. In an exemplary embodiment, the influx of blood cells can occur into the entire cochlea. Accordingly, this can change the slopes/curves of the voltage plots/electrical phenomenon plots. A whole change/change in the entire curve for one temporal location to another temporal location can be indicative of such trauma. That is, by analyzing the entire curve, it can be deduced the type of damage that has occurred. This can be contrasted to, for example, where a local change has occurred in the curve. That is, the entire curve has not changed, but only a portion thereof. This increase in the local gradient could potentially indicate where the influx is located. In an exemplary embodiment, by taking the second derivative of the curve, second spatial derivatives of the cochlear voltage tradition or otherwise the electrical phenomenon distribution, a specific location of the occurrence of damage and/or the occurrence of a given phenomenon, relative to location along the electrode array, can be determined. In some embodiments, this can be done in real time and/or quasi-real time. In an exemplary embodiment, in response to the detection of such an influx of blood or immune system response to injury the surgeon or clinician can respond, for example by administering, either topically or systemically, anti-inflammatory agents such as dexamethasone.

In an exemplary embodiment, electrical pulses are utilized to provide the current to the electrode. The electrical pulses can be the same as the electrical pulses that are utilized to evoke a hearing percepts while in other embodiments, these can be different. By way of example only and not by way of limitation, longer pulses than those utilized to evoke a hearing percepts can be utilized. In an exemplary embodiment, pulses having a length of 1 ms can be utilized. In an exemplary embodiment, in view of the different cell types that can exist or otherwise be present in the cochlea as a result of damage or as a result of a given phenomenon occurring in the cochlea, lower frequency/longer pulses can be utilized. In an exemplary embodiment, the current is decreased and the frequency is decreased and the length of the process is increased to, for example, 1 ms, all relative to that which would be the case when utilizing the cochlear implant/electrode to evoke a hearing percept.

As just noted, in some embodiments, there are different types of cells that can exist in the cochlea that may or may not be transparent or otherwise hard to "see" utilizing the teachings detailed herein. In this regard, in an exemplary embodiment, a pulse length of current to apply to an electrode can be increased by more than 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 90, 100, 125, 150, 175, 200, 250, 300, 350, 400, 500, 600, 700, 800, 900, 1000 or more times relative to that which would be utilized during a normal cochlear implant utilization to evoke a hearing percept (e.g., 25 microseconds). In an exemplary embodiment, the frequency is reduced by in some instances, about the same amount as the pulse length is increased.

It is also the case that in some exemplary embodiments, the current can be increased or decreased to highlight different types of cells. In an exemplary embodiment, the current can be decreased by more than 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 90, 100, 125, 150, 175, 200, 250, 300, 350, 400, 500, 600, 700, 800, 900, 1000 or more times relative to that which would be utilized during a normal cochlear implant utilization to evoke a hearing percept (e.g., 18 μA). That said, in an alternate embodiment, the current can be increased by the aforementioned amounts relative to that which would be utilized during a normal cochlear implant utilization to evoke a hearing percept (which could be 1.8 μA in some embodiments, while in other embodiments, it is 18 μA).

In an exemplary embodiment, amperage is increased with increasing pulse length, relative to that which would be utilized during normal operation of the cochlear implant to evoke a hearing percept. In an exemplary embodiment, amperage is decreased with increasing frequency, again relative to that which would be utilized during normal operation of the cochlear implant to evoke a hearing percept.

In an exemplary embodiment, the longer pulse length and/or the different frequencies and/or the different amperage can highlight different cells/see cells that would otherwise be invisible at the same pulse lengths. In this regard, the curves of the voltages/electrical features may be different depending on the length and/or frequency and/or amperage that is utilized. That is, a curve could look perfectly normal when the curve is produced utilizing certain lengths and/or amperage and/or frequencies, while the curve could look abnormal utilizing others, and thus the teachings detailed herein can utilize the different lengths and/or frequencies and/or amperage is to identify he existence of a damage condition. To be clear, if there was no damage, in at least some embodiments, the curves would look the same irrespective of the length and/or frequencies and/or amperages.

In at least some exemplary embodiments, the teachings detailed herein can be utilized to identify the occurrence of an immune cascade. By evaluating the first and second spatial derivatives of the curve, the existence of an immune cascade can be identified. In an exemplary embodiment, upon such identification, and a method of fitting the cochlear can include flushing the cochlea and/or applying medicine. Is also noted that by evaluating the curves, it is possible to determine whether or not the damage condition is local and more widespread. Again, evaluating the first and/or second derivatives of the curves, can provide an indication as to whether or not the trauma is local or widespread, and based on the determination, the treatment can be handled in a different manner.

It is noted that at least some exemplary embodiments can evaluate the so-called trans-impedance associated with the electrode array. Conversely, some embodiments herein explicitly do not utilize trans-impedance associated with the electrode array.

The teachings detailed herein can be utilized to tell the difference between fibrous tissue growth versus normal tissue, fibrous tissue growth vs. bone, membrane, hair, etc., or otherwise non-fibrous tissue growth. The teachings detailed herein can be utilized to tell the difference between a degree of fibrous tissue growth that is indicative of something that is not desired vs. something that is normal or otherwise within acceptable parameters. By varying the pulse widths according to the teachings above, different types of tissue can be identified. Some tissue is tissue consistent with normal growth, and thus does not represent a deleterious condition, where as other tissue does represent a deleterious condition. By varying the features of the current applied to the electrode, different types of tissue can be identified (or not identified). This can enable the healthcare professional to determine what is going on in the cochlea, and whether or not such represents a deleterious condition. Of course, consistent with the teachings detailed above, the speed at which certain changes occur within the cochlea can be indicative of a deleterious condition. Thus, the teachings detailed herein include the action of taking repeated measures according to the teachings detailed herein, and evaluating those measures.

FIG. 9 presents another algorithm for an exemplary method, method 900. Method 900 includes method action 910, which includes applying electrical current to an electrode located in a cochlea of a recipient. Method 900 includes method 920 includes the action of obtaining data indicative of electrical properties at a plurality of locations away from the electrode. Method 900 includes method action 930, which includes evaluating electrical conductivity between the electrode and the plurality of locations based on the obtained data. Method 900 also includes method action 940, which includes determining whether or not a phenomenon exist in the recipient based on spatial derivatives between the electrode in the locations. This latter action is consistent with the teachings detailed above. Also consistent with the teachings detailed above, any locations that can enable the teachings detailed herein can be utilized. For example, the locations can be, in an exemplary embodiment where the stimulating electrode is electrode 10, locations at the electrodes 11, 12, 13, 14, 15, and locations at the electrodes 9, 8, 7, 6, 5 and so on. In an exemplary embodiment, the spatial derivatives can be average spatial derivatives, etc. In an exemplary embodiment, locations can be skipped. For example, the spatial derivative can be the derivative between, for example, locations 12 and 13, locations 11 and 14, location locations 13 and 15, etc.

It is noted that in an exemplary embodiment, the teachings detailed herein can be utilized to evaluate the quality or the efficacy of the seal at the cochleostomy. In this regard, embodiments herein are such that the impedance of the cochleostomy seal will affect the current flowing in the scalae and hence the first derivative of measured voltages at the read electrodes. A good cochleostomy seal will reduce the current required to stimulate the auditory nerve. In some embodiments, this is a feature that the surgeon implanting the electrode array in the cochlea will seek to optimize during surgery. Accordingly, in an exemplary embodiment, there is a method that includes providing a voltage gradient to the surgeon, in some instances, in real time, and the surgeon adjusting his or her actions so as to optimize the sealing of the cochleostomy or otherwise improve the sealing of the cochleostomy relative to that which would be the case in the absence of the provided voltage gradients. Thus, in an exemplary embodiment, the action of determining whether or not a phenomenon exists in the recipient includes determining whether or not a phenomenon exists at boundaries of the cochlea based on the evaluation. Accordingly, getting back to method 900, in an exemplary embodiment, the phenomenon is a sealed cochlea at a location through which an electrode array assembly extends from outside the cochlea to inside the cochlea. This as opposed to a phenomenon of a non-sealed cochlea or a partially sealed cochlea. Thus, in an exemplary embodiment, the phenomenon can be a non-sealed cochlea or a partially sealed cochlea at a location through which an electrode array assembly extends from outside the cochlea to inside the cochlea.

Indeed, in view of the above, it can be seen that in some embodiments, the action of applying electrical current and obtaining the data and evaluating is executed during a cochlear implant electrode array surgery, and the method further includes adjusting a seal at a location through which the electrode array assembly of the cochlear implant extends from outside the cochlea to inside the cochlea based on the determination. Further, in some embodiments, the action of applying electrical current and obtaining the data and evaluating is executed during a cochlear implant electrode array surgery in real time during the surgery. In some embodiments, the phenomenon is a completely sealed cochlea, and in other embodiments, the phenomenon is a non-completely sealed cochlea. In an exemplary embodiment, the phenomenon is an extent of sealing at a cochleostomy or a window of the cochlea through which a surgical incision has been executed.

In an exemplary embodiment, the lack of a seal/lack of a sufficient seal at the cochleostomy or at the basil region will produce a gradient spike on the basil side of the stimulating electrode which will not be present or otherwise will not be as significant on the opposite side of the electrode. Accordingly, by comparing the two sides of the skirt about the electrode, a determination can be made regarding the quality of the presence of the seal at the basil end.

Note also that in at least some exemplary embodiments, the teachings detailed herein can be utilized to identify whether or not the electrode array has migrated. In an exemplary embodiment, movement of the electrode array will cause an opening, however slightly, at the location where the electrode array extends into the cochlea. This will cause a basil gradient spike. This may later return to normal, as the location where the array enters the cochlea reveals. By identifying this later return to normal, it can be determined that the spike was the result of electrode migration, or at least inferred that such is the case. In an exemplary embodiment, the lower the amount of current that flows through the seal, the higher the gradients will be at the location proximate the seal/at the locations of the skirts between the electrode and the seal, and vice versa. Accordingly, embodiments are directed towards methods that include identifying this phenomenon, and determining or at least inferring features/phenomenon about the seal based thereon and/or about the electrode array extending through the seal. That is, in some embodiments, the methods can be directed towards identifying an increase and/or a decrease in the current gradient on the basil side of the skirt.

In some exemplary embodiments, the phenomenon of method 940 is the presence of perilymph at the electrode. In this regard, it is noted that in at least some exemplary embodiments, the location of the electrode that is stimulated can have a bearing on whether or not the electrode is located in perilymph. In an exemplary embodiment, in some scenarios of implantation, the electrodes that are located at the beginning of the cochlea are in perilymph, and the electrodes further into the cochlea are not in perilymph. This could be, in an exemplary embodiment, due to the fact that perilymph has leaked from the cochlea. In this regard, in an exemplary embodiment, the electrode is located past at least one of the 90, 105, 120, 135, 150, 165, 180, 195, 210, 225, 240, 255, 270, 285, 300, 315, 330 degree turn of the cochlea, and the phenomenon is the presence of perilymph at the electrode. In an exemplary embodiment, the phenomenon is the presence of perilymph at one electrode and not the presence of perilymph and another electrode. In an exemplary embodiment, the electrode is an electrode of a cochlear electrode array located in the cochlea, and the electrode is one of the apical electrodes of the electrode array.

The teachings detailed herein vis-à-vis the determination of the electrical characteristics of the various locations can be utilized to, in some embodiments, determine the spatial positioning of the electrode array and/or determine that the electrode array has moved relative to a prior location. In an exemplary embodiment, the teachings detailed herein can be utilized to determine a distance or otherwise estimated distance from one of the walls of the cochlea, such as, for example, modiolar wall and/or the lateral wall.

Figure 10:
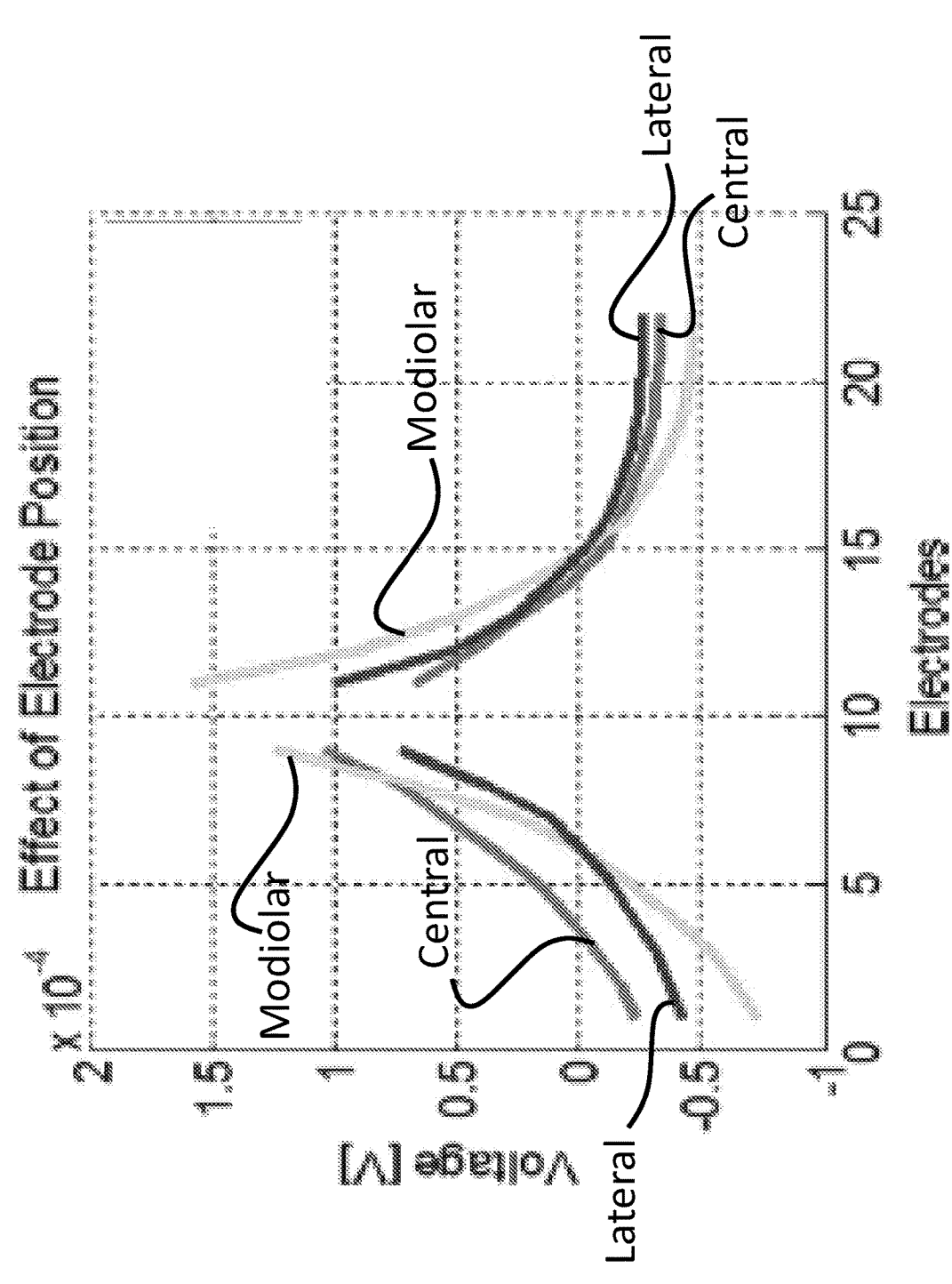

FIG. 10 presents exemplary hypothetical voltages for three different electrode positions within the scala tympani. As can be seen, there is a distinct difference between the three different curves for the three positions. Accordingly, by evaluating the first spatial derivative of the voltage distribution (or other electrical property distribution that may be utilitarianly evaluated), the voltage gradient can be utilized, in some instances, in real time, as a measure of the electrode-modiolus distance or electrode lateral wall distance, or any other spatial distance that can be utilitarian for evaluating an orientation of the electrode array.

By way of example only and not by way of limitation, in an exemplary embodiment, the aforementioned distance determinations can be utilized during insertion of the electrode array and/or during a fitting process. With respect to insertion, there can be utilitarian value with respect to determining the distance so as to determine whether or not a so-called crawled electrode array is fully inserted. In this regard, the apical and of the electrode array will fit snugly against the modiolus wall of the cochlea at full insertion. Conversely, prior to full insertion, the tip of the electrode array will be in contact with the wall, but the electrodes away from the tip will be raised a bit because the curvature of the electrode array does not correspond to the curvature of the wall (the radius of curvature is a different). Accordingly, the distance from the modiolus wall can be utilized to determine whether or not the electrode array is fully inserted or otherwise to determine that the electrode array should not be inserted further into the cochlea or otherwise determine that the insertion process should be stopped. In an exemplary embodiment, by determining the distance from the electrodes of the electrode array to the cochlea wall, if the distances are approximately the same or otherwise the same, a determination can be made that the electrode array is fully inserted into the cochlea. It is noted that in an exemplary embodiment of this embodiment, only some of the electrodes are utilized for measurement purposes. This is because, for example, in this exemplary embodiment, the distances of the most apical electrodes are the only ones that are important or otherwise are the ones that can provide the information as to whether or not the electrode array is fully inserted. Accordingly, processing power and/or the rate of stimulation can be increased because only a few electrodes are at issue.

Conversely, in an exemplary embodiment, in a fitting scenario, more than just a few of the electrodes are utilized.

Indeed, in an exemplary embodiment, all of the electrodes are utilized or otherwise most of the electrodes of the electrode array utilized. This is because there can be utilitarian value with respect to determining the distance of each electrode or many of the electrodes respectively, from the wall of the cochlea for fitting purposes. Moreover, more precise measurements can be utilitarian with respect to fitting, whereas more general measurements can be utilized to determine whether or not the electrode array is fully inserted into the cochlea. In an exemplary embodiment, the gradients utilize detailed herein can be utilized in both the fitting in the insertion methods. In an exemplary embodiment, the gradients utilize herein can provide a better resolution than the utilization of raw impedance measurements. In an exemplary embodiment, the resolution is 50%, 75%, 100%, 100 of the present, 200%, 250%, 300%, 400%, 500% or more utilizing the gradients as opposed to the utilization of the impedance measurements.

In an exemplary embodiment, the measurements are taken sequentially along the electrode array, and in some embodiments, along the full length of the electrode array.

In an exemplary embodiment, the gradient trends are compared so as to determine the distance from the modiolus wall. In an exemplary embodiment, as noted above, the first derivative is utilized. In an exemplary embodiment, a second derivative is utilized. Note that the second derivative can be a temporally consistent derivative. In this regard, the rate of change of the change, instantaneously, is evaluated. Accordingly, in an exemplary embodiment, the second derivative is taken or otherwise obtained while the electrode array is stationary and otherwise not moving in the cochlea. This as opposed to obtaining a second derivative that is time-based.

In view the above, in an exemplary embodiment, the second derivative can entail comparing the gradient between two electrode pairs to the gradient between two other electrode pairs, and evaluating the change in the gradient. This can be done repeatedly for any number of electrode pairs. Utilizing the second derivative, phenomenon associated with the electrode array can be determined.

In an exemplary embodiment, the data can be simply displayed in real time, without any processing. The surgeon can interpret the data visually/mentally. That said, in an exemplary embodiment, a heat map or the like can be applied, showing the derivative/gradient. In this regard, a computer that is programmed to evaluate the data can be utilized to highlight changes in the curve that could be indicative of the phenomenon that is desired to be identified.

In some embodiments, an image of the cochlea can be presented on a computer monitor. That is, a view of the cochlea can be presented. In an exemplary embodiment, the data can be evaluated, and if, for example, in aberrant occurrence of the data is present, such as, for example, data indicating a rapid increase in impedance, this can be shown on the monitor. Depending on the methods utilized to evaluate the data, the specific location within the cochlea, based on the location of the electrode array, can be shown on the monitor. In this regard, it is noted that in at least some exemplary embodiments, there is a feedback mechanism or otherwise a device, system and/or method of monitoring the position of the electrode array in the cochlea. For example, the insertion tool can be configured with a device, such as a sensor, that senses the electrodes as they pass by the sensor, thus estimating the depth of insertion of the electrode array. This depth of insertion can be correlated to the image of the cochlea, and based on the data, the phenomenon can be localized and presented on the screen goes on to the cochlea.

Note also that temporal changes of the spatial derivative changes can be utilized in some embodiments. For example, in an exemplary embodiment, where, for example, a wall of the cochlea is punctured, as blood spreads into the cochlea, the derivatives will change. If the data is collected quickly and/or repetitiously enough, a reverse analysis can be executed to localize or otherwise determine where the blood introduction occurred. By rough analogy, this could be like analyzing a spread of a stain on a tablecloth to identify where a glass of wine was located that ultimately spilled.

In this regard, in an exemplary embodiment, there is a method as detailed above and/or below, wherein the action of determining whether or not a phenomenon exists in the recipient includes determining that the phenomenon exists, the electrode is an electrode array of a cochlear implant implanted in the recipient. Also, the method further comprises comparing respective spatial derivatives of voltages centered at a plurality of respective spatial locations along the electrode array and determining localized changes within the cochlea based on the comparison. In this regard, in some embodiments, there is the action of comparing spatial derivatives centered at a plurality of spatial locations to determine localized changes within the cochlea. By way of example only and not by way of limitation, in an exemplary embodiment, anomalous spatial derivatives or otherwise data indicating that a given phenomenon exists can be found at some locations along the electrode array but not others, or a change or a rate of change, etc., associated with the data at one local location can be indicative of a phenomenon, while the change or rate of change etc., associated with the data at another location can be indicative that the phenomenon does not exist or otherwise that the phenomenon is not as pronounced at that location relative to the other location. Moreover, the change or rate of change in the data at given locations can be utilized to determine the timing of a spread of the phenomenon, which, based on the timing of the spread of the phenomenon, can be utilized to determine what type of phenomenon is occurring and/or what type of phenomenon is not occurring.

Accordingly, in an exemplary embodiments of method 900, the phenomenon of method action 940 is a proximity of the electrode to a wall of the cochlea. Still further, in an exemplary embodiment of method 900, the phenomenon is a proximity of the electrode to the modiolus of the cochlea and/or the lateral wall of the cochlea. Also, in an exemplary embodiment of method 900, the phenomenon is a determination as to whether or not the electrode array is in contact with any of the walls over some or all of the length thereof. Indeed, in an exemplary embodiment, the evaluated derivatives can indicate that some electrodes are positioned at one orientation (e.g., centrally located between the walls), and other electrodes are positioned at another orientation (e.g., against one of walls, such as the modiolus wall and/or the lateral wall). In an exemplary embodiment, the phenomenon of method action 940 is a determination as to whether or not one or more or all of the electrodes are located proximate the modiolus wall, the lateral wall, or are centrally located. Any arrangement of positioning that can be determined can be utilized in at least some exemplary embodiments.

In view of the above, it is to be understood that by providing a measure of the gradient to the surgeon during electrode insertion, in some embodiments, such can assist the surgeon with placing the electrode(s)/electrode array, in a peri-modiolar position, in a central position or in a lateral wall position. Again, modiolar proximity can vary along the length on an array. In at least some exemplary embodiments, the data that is relied upon to determine position can be the data that corresponds to the gradient adjacent or near to the simulating electrode. The data from other electrodes can be discounted. In this regard, this method and/or for other methods, electrode array having 10, 16, 22, 30, 50, etc., or for an electrode array having between 4 and 100 electrodes, the gradients of any combination can be included and/or discounted. That is, any of the gradients between electrodes X and Y can be utilized and/or discounted, wherein X and Y are integer values between 1 and the maximum number of electrodes in the array, which can be, in some embodiments, any integer value between 1 and 100.

In an exemplary embodiment, different stimulating electrode positions can be used during the electrode insertion and the gradient can be measured at the same distance from the stimulating electrodes on one or more all of the respective occasions. In at least some exemplary embodiments, this can provide utilitarian value in that such can provide a more reliable measure of proximity than that which may be the case by measuring the gradient from just one stimulating electrode position.

In view of the above, FIG. 11 presents an exemplary algorithm for an exemplary method, method 1100. Method 1100 includes method action 1110, which includes applying an electrical current to an electrode located in a cochlea of a recipient. This can be done according to any of the teachings detailed herein and/or variations thereof, and any other way that can enable the utility of the teachings detailed herein. Method 1100 also includes method action 1120, which includes the action of obtaining data indicative of electrical properties at a plurality of locations away from the electrode. This can be any of the read electrodes of the electrode array, by way of example. Method 1100 also includes method action 1130, which includes the action of determining a spatial locational feature of the electrode within the cochlea relative to an anatomical structure of the cochlea based on a gradient of the obtained electrical properties.

In an exemplary embodiment, the spatial locational feature is a proximity of the electrode to a modiolus of the cochlea. By proximity to a modiolus of the cochlea, this includes both a binary determination that the electrode is/is not proximate, a determination of a distance, or a determination that the electrode is proximate another structure which would rule out proximity to the modiolus.

In an exemplary embodiment, consistent with the embodiment of FIG. 1, the electrode is an electrode array of a cochlear implant. Further, the locations are locations location of other electrodes of the electrode array (e.g., a read electrode). Also, the spatial locational feature is a classification of electrode array positioning from a group consisting of modiolar positioning, central positioning and lateral positioning. In some embodiments of the method of method 1100, again, the electrode is an electrode array of a cochlear implant, the location is a location of another electrode of the electrode array, and the spatial locational feature is a classification of electrode array positioning from a group consisting of modiolar positioning, central positioning and lateral positioning.

In an exemplary embodiment of method 1100, there includes the additional action of comparing the gradient obtained in method action 1120 to a database of gradients. The gradient obtained in method action 1120 and the database of gradients can be normalized to compensate for anatomical variation, measurement variation and/or other discrepancies in the data. In an exemplary embodiment, this database can be based on empirical data and/or analytical data. Any data that can be utilized to implement the teachings detailed herein can be utilized. Further, based on the comparison, a determination that the electrode array is positioned in one of the three classifications is made. The database can include numerical and/or graphical data an exemplary embodiment, the data obtained regarding the plurality of locations away from the electrode can be plotted on a computer screen or the like, and superimposed thereon can be the graphical representations from the database for different location classifications. In an exemplary embodiment, the surgeon or other healthcare professional can look at the curves and determine which of the curves most closely corresponds to the results from the electrode array implanted into the recipient at that time. Based on the determination, a determination can be made as to the positioning of the electrode array. Alternatively, and/or in addition to this, this process can be automated. An intelligent system or the like can evaluate the curves, and determine which one has similarities that render it closest to the other curve. That said, in an alternate embodiment, the raw data/raw numbers can be analyzed automatically and compared to numbers in a database, which numbers can correspond to one of the classifications. Note further, in an exemplary embodiment, the database need not necessarily include hard numbers, but instead can include data indicators, where, if present in the data obtained indicative of the electrical properties of the plurality of locations, a determination can be made that the electrode array is in one of the three classifications.

Note also that the aforementioned database can be utilized to provide actual distance values. In an exemplary embodiment, the database can include data that is correlated to distances for the various walls, and based on the data, a determination of distance can be determined.

Thus, in another exemplary implementation of method 1100, again, for example, where the electrode is an electrode array of a cochlear implant, and again, where the locations are locations of other electrodes of the electrode array other than that to which current is applied, the method further comprises comparing the gradient to a database of gradients, and, based on the comparison, determining a position of the electrode array relative to a modiolus of the cochlea based on a steepness of the gradient relative to gradients of the database of gradients. By steepness, it is not meant that this requires a graphical representation. Instead, this is meant in terms of a quantifiable result that has meaning. By way of example only and not by way of limitation, the steepness of a Dow Industrial Average increase or decrease need not be presented graphically. Indeed, people can refer to steep declines or steep increases in the value of something.

In some embodiments, the method further comprises comparing the gradient to a database of gradients, and based on the comparison, determining that the electrode array is positioned in a perimodiolar location based on the fact that the gradient has a steepness that is different than gradients of the database of gradients for other types of electrode array positioning. In an exemplary embodiment, as noted above, the gradients can be gradients associated with the locations closest to the stimulating electrode (e.g., the locations of the closest 2, 3, 4, 5 or 6 electrodes on either side of the electrode array). Again, in some embodiments, some of the locations can be discounted out right. Conversely, in some embodiments, average steepness can be utilized. In some embodiments, the electrode is an electrode array of a cochlear implant, the action of applying electrical current and obtaining the data is executed during a cochlear implant electrode array surgery of the electrode array into the cochlea, the method further includes adjusting a position of the electrode array based on the determined spatial locational feature. By way of example only and not by way of limitation, in an exemplary embodiment, after any one of the electrodes of the electrode array has been inserted into the cochlea (e.g., any one or more of electrodes 1 to 22 or 1 to 100 or any value or range of values therebetween in 1 increment), method 1100 or a portion thereof and/or the other method actions detailed herein can be executed for one or more of the electrodes inserted into the cochlea, such as, for example, the action of stimulating a given electrode and obtaining the data for the other electrodes, and determining the spatial locational feature at that time. This can be done incrementally for each electrode, or in groups of electrodes, etc. Indeed, the determination as to when to execute some of the actions detailed herein can be based on intuition or otherwise based on the surgeon's feel for what is going on. By way of example only and not by way of limitation, the surgeon might estimate that the positioning of the electrode array is not what he or she desires, and thus execute the methods herein to determine the location of the electrode array/confirm the surgeon's suspicions. Conversely, the surgeon can utilize the teachings detailed herein to confirm or otherwise ensure that the location of the electrode array is where he or she believes the electrode array to be.

The action of adjusting the position of the electrode array can occur many times during an insertion operation. In an exemplary embodiment, the surgeon can fully insert the electrode array, and then utilize the teachings detailed herein to determine the position, etc., and then reposition the electrode array based on the determinations.

In view of the above, it is to be understood that the teachings detailed herein can be executed in real time, while the operation is occurring, and can also be executed before the final closing of the incision to perform the electrode array is executed. Thus, the action of applying electrical current and obtaining the data and determining the spatial locational feature is executed during a cochlear implant electrode array surgery in real time during the surgery. Note also that in at least some exemplary embodiments, the teachings detailed herein can be utilized after implantation/after completion of the surgery, such as by days or weeks or months or even years after the completion of the surgery, to determine whether or not the electrode array has moved in the intervening period.

Consistent with the above-detailed embodiment where the various method actions are executed more than one time for different electrodes where the stimulating electrode is changed (e.g., electrode 11, 10, 9, 8, and then 7, for example, where electrode 11 is the most apical electrode), in an exemplary embodiment, there is an exemplary method, method 1200, which includes method action 1210, which includes executing method 1100. Method 1200 also includes method action 1220, which includes applying respective currents to respective electrodes of a plurality of electrodes of the electrode array located in the cochlea of a recipient other than that to which the current was previously applied. Again, in an exemplary embodiment, where, for example, when executing method 1100, the stimulating electrode was electrode 10, these plurality of electrodes can be electrodes 8 and 6, for example (note also that in some other embodiments, only one more electrode is stimulated, while in other embodiments, three or four or five or six or seven or eight or nine or 10 or 11, or 12, or 13 or 14 or 15 or more electrodes are stimulated). Method 1200 also includes method action 1230, which includes obtaining respective data indicative of electrical properties at respective plurality of locations away from the respective electrodes to which respective currents are applied. Again, these can be any number of read electrodes, and can, in some embodiments, constitute an electrode that was the electrode to which current was supplied when executing method 1100. In some embodiments, there is utilitarian value with respect to obtaining data for all of the locations that can be utilized as read electrodes, while in other embodiments, such as for purposes of efficiency or speed, only some of the electrodes are utilized as read electrodes (e.g., only 2, 3, 4, 5, 6, 7, 8, 9, 10, 11, 12, 13, 14, 15, 16, 17, 18, 19, 20, etc., are utilized). Note also that the same electrodes need not necessarily be utilized as read electrodes when executing method action 1230 for other stimulating electrodes. For example, if electrodes 13 and 14 are utilized as read electrodes when electrode 10 is stimulated, one or both of those electrodes may or may not be utilized as read electrodes when electrode 9 or 11 or 12, for example is utilized as the stimulating electrode.

Method 1200 also includes method action 1240, which includes determining a spatial locational feature of one or more of the electrodes to which current was applied other than that to which the current was previously applied relative to an anatomical structure of the cochlea based on respective gradients of the obtained electrical properties at the respective plurality of locations away from the respective electrodes. In an exemplary embodiment, the gradients between the locations, or at least some of them, can be evaluated to determine the spatial locational features.

Note also that in a variation of method 1200, the actions associated with determining the spatial locational features are replaced with determining or otherwise identifying any of the other identified phenomena herein. Note also that the methods herein are not mutually exclusive. Method 1200 can be executed to determine the spatial locations as well as to determine whether or not damage exists, etc., or otherwise evaluate any of the phenomenon detailed herein or other phenomenon for that matter.

In view of the above, it can be seen that at least some exemplary embodiments have utilitarian value with respect to utilizing the first spatial derivative of the cochlear voltage distribution curve. In at least some exemplary embodiments, such can be utilized or is utilized to protect one or more of connectivity changes of Paralympic and/or tissue in the scalae, growth of fibrous tissue in the scalae, the existence and/or the extent of ceiling of a cochleostomy, round window, oval window, or any other opening in the cochlea, proximity of the electrode array to the modiolus or lack thereof, or to another wall. Also, as will be described below, such can be utilized to predict locality of impedance change.

It is also noted that in some embodiments, a second spatial derivative is utilized of the cochlear voltage distribution curve to protect one or more or all of the above.

It is noted that method actions 1220 and 1230 and 1240 need not be executed in a stepwise fashion, as is with the case with respect to any of the methods detailed herein. For example, action 1220 can be executed partially by applying stimulation to one other electrode, and then obtaining the respective data in method action 1230 and then executing method action 1244 that one electrode, and then applying stimulation to yet another electrode, thus satisfying method action 1220, and then obtaining the respective data in method action 1230, thus satisfying method action 1230, and then executing method action 1244 that data obtained in method action 1230. Indeed, to be clear, unless otherwise specifically stated, any of the method actions can be executed in whole or in part in any order with respect to any of the other method actions detailed herein providing that the art enables such. In this regard, FIG. 13 presents an exemplary algorithm for an exemplary method, method 1300, which is presented in more of a stepwise, discrete fashion. It can be seen that method action 1320 is executed for one specific electrode, and method action 1330 is executed based on that one specific electrode of method action 1320. In method 1300, N equals 1 when executing method action 1310. After executing method action 1330 (for thus N+1, where N would now equal 2), the method then returns back to 1320 for another electrode, which would be electrode N equals 3 (owing to N+1 where N was 2), and so on. In an alternative embodiment, method action 1340 is executed after executing method action 1330, and then the process returns back to 1320 for a new electrode, and so on. In an exemplary embodiment, and his any integer between 1 and 100 in 1 integer increments.

Note that the numerical value for the electrodes here is not necessarily specific to a given channel number. For example, it could be that the first electrode that is the subject of method action 1310 is electrode 22, and then the process works backwards.

In an exemplary embodiment, the locations for method action 1330 can be any one or more of N+1, N+2, N+3, N+4, N+5, N+6, N+7, N+8, N+9, N+10, N+11, N+12, N+Y, and/or N−1, N−2, N−3, N−4, N−5, N−6, N−7, N−8, N−8, N−10, N−11, N−12, and/or N−Y, where Y is any integer value between 13 and 100, etc.

Figure 14:
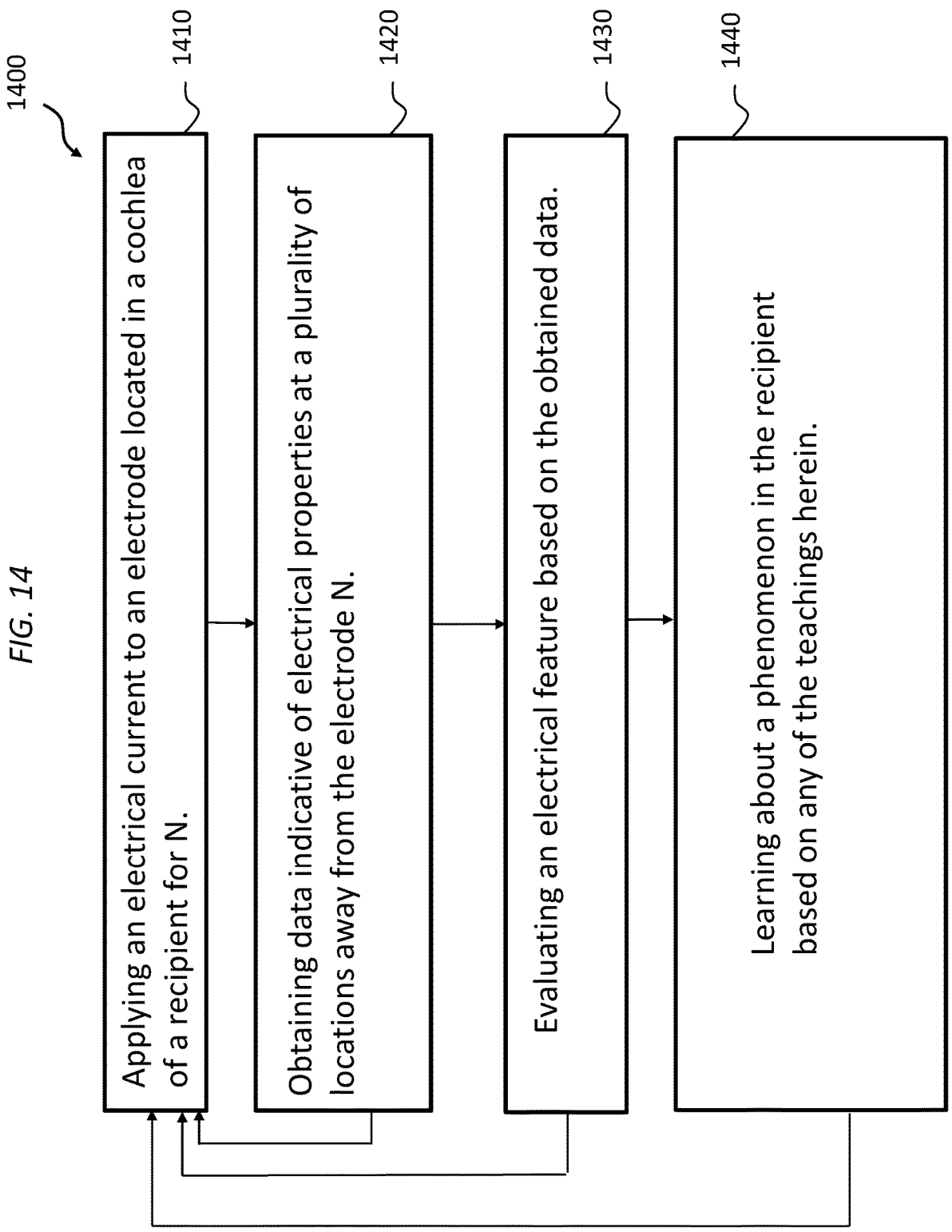

FIG. 14 presents an exemplary algorithm for an exemplary method, method 1400, which is presented in more of a stepwise, discrete fashion than those detailed above. FIG. 14 represents an algorithm for a quasi-generic method of implementing any of the actions detailed herein. In this regard, method 1400 includes method action 1410, which includes applying an electric current to an electrode located in a cochlea of a recipient for N, where, at the beginning of the method, and equals 1, and the electrode corresponds to the N value. Method action 1420 entails obtaining data indicative of electrical properties at a plurality of the locations away from the electrode N. In an exemplary embodiment, the locations for method action 1420 can be any one or more of N+1, N+2, N+3, N+4, N+5, N+6, N+7, N+8, N+9, N+10, N+11, N+12, N+Y, and/or N−1, N−2, N−3, N−4, N−5, N−6, N−7, N−8, N−8, N−10, N−11, N−12, and/or N−Y, where Y is any integer value between 13 and 100, etc. Method 1400 also includes method action 1430, which includes evaluating an electrical feature based on the obtained data obtained in method action 1420. Method action 1440 entails learning about a phenomenon in the recipient based on any of the teachings detailed herein. As can be seen, the method can be executed in a variety of orders. In any event, upon the return to method action 1410, 1 is added to N, and thus the second time method action 1410 is executed, that is for electrode number 2 (where again, that is simply an accounting name for the electrode, and need not necessarily correspond to the exact number of the electrode—N equals 1 could be electrode number 10 of a cochlear electrode array, for example). In some embodiments, machine learning can be utilized. For example, example data sets can be used to train a machine leaning algorithm, such as by using expert human analyzers to classify each dataset into a number of categories. After training, the machine can then be used to classify future datasets, in real time if such is utilitarian, providing an interpretation of a particular dataset. This can be useful for reducing any need for advanced training for clinicians in the art of determining potential issues based on measured datasets.

It is noted that in an exempalry embodiment, the methods 1300, 1400 and/or 1500 can be reputedly executed multiple times per day, per week, per month and/or per year. As will be detailed, in some embodiments, these methods can be executed autonomously by the cochlear implant system. In some embodiments, these methods are executed 1, 2, 3, 4, 5, 6, 7, 8, 9, 10, 11, 12, 13, 14, 15, 16, 17, 18, 19, or 20 times or more per X hours, X days, X weeks, or X months and variations thereof.

It is noted that in some embodiments, the gradient(s) adjacent to the stimulating electrode can, in some instances, be utilitarian in that it can be the most sensitive parameter to reflect proximity (e.g., proximity to one of the walls detailed herein). The average of the gradients immediately adjacent to and either side of the stimulating electrodes can be utilized as a proxy. In other words, for stimulating electrode N, the value for proximity measure, M, could be derived as follows:

$$M=[(V_{N+1}-V_{N+2})+(V_{N-1}-V_{N-2})]/2$$

Thus, in an exemplary embodiment of method 1100 where the electrode is an electrode array of a cochlear implant, and where the locations are locations of other electrodes of the electrode array than the electrode to which current is applied. In this exemplary embodiment, the method further comprises deriving a proximity proxy value by averaging a gradient of the obtained electrical properties for electrodes immediately adjacent the electrode to which current is provided, wherein the action of determining the spatial locational feature is based on the derived proximity proxy value.

Figure 15:
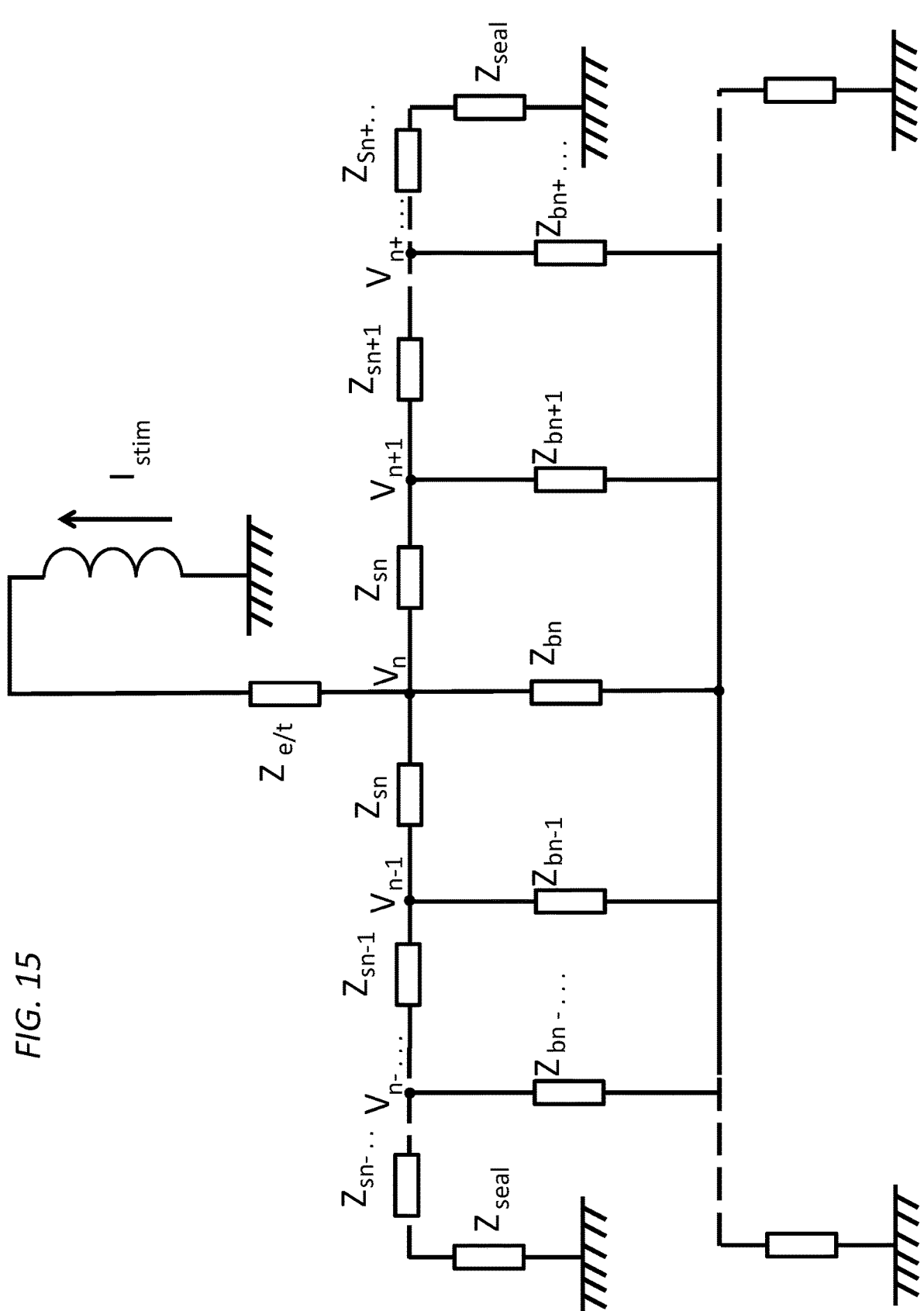
FIG. 15 presents a conceptual schematic applicable to the teachings herein.

FIG. 15 presents a conceptual schematic circuit representation of the cochlea and the surrounding bone/tissue thereof. This is a simplified version of the lumped parameter model proposed in Susserman (1993) IEEE Trans. BME 40, 237-245. Each node on the model (n, n+1 etc.) represents the position of one electrode along the cochlear scalae. The impedances marked $Z_{sn}$, $Z_{sn+1}$, etc. represent the impedance between electrodes within the cochlea scalae. These impedances can be primarily determined by the conductivity of the perilymph and, in some instances, any fibrous tissue within the scalae and, in some instances, by the geometry of the scalae in the region of electrode n (same as upper case N above). The proximity of the electrode to structures within the cochlear such as the modiolus can also be a factor in determining the value of $Z_{sn}$, $Z_{sn+1}$, etc. The impedances $Z_{bn}$, $Z_{bn+1}$, etc., are the impedances of the bone and/or other tissue of the otic capsule which surrounds the cochlear scalae. Generally the values of $Z_b$ are many times larger than the values of $Z_s$. Current is delivered at electrode n and is labelled $I_{stim}$. in FIG. 15. The impedance of the electrode/ tissue interface ($Z_{e/t}$ in FIG. 15) can be significant but also appears in series with the electrode and therefore can add a constant offset to all values of $V_n$. The first derivative of voltage $V_n$, as detailed above, can be a utilitarian diagnostic measure, and, in some embodiments, this is not affected by a constant offset added to all values of $V_n$. Hence, the series impedance of the electrode/tissue interface is ignored in some embodiments.

In view of the above, in an exemplary embodiment, for electrode n=1, to which current is applied according to the methods detailed above, the voltage gradient could be the voltage gradient between $V_{n+1}$ and $V_{n+2}$, between $V_{n+2}$ and $V_{n+3}$, between $V_{n-1}$ and $V_{n-2}$, between $V_{n-2}$ and $V_{n-3}$ etc. based on these measures, it is possible to infer the values of $Z_{sn}$ . . . .

It is noted that in some embodiments, the electrode stimulated/the electrode connected to the $I_{stim}$ (where $I_{stim}$ is applied to the various nodes/electrodes V) cannot be utilized as the read electrode. Indeed, note that the voltage at the stimulating electrode in FIG. 5, FIG. 7, which includes a voltage drop across the stimulating electrode, is not plotted. However, there is utilitarian value with evaluating the impedance associated with the stimulating electrode.

In view of the above, in an exemplary embodiment, can be seen that at least some of the methods detailed herein include the action of specifically ignoring the value of the impedance of the stimulating electrode ($Z_{e/t}$). Accordingly, any of the teachings detailed herein can be executed by ignoring such. That said, in at least some alternative embodiments, the value of the stimulating electrode can be estimated. The value of $Z_{e/t}$ is the impedance associated with the electrode/tissue interface and the tissue and perilymph in the close vicinity of the stimulating electrode.

In an exemplary embodiment, the vicinity, which may or may not be a close vicinity, is within a distance of 0.02, 0.04, 0.06, 0.08, 0.1, 0.2, 0.3, 0.4, 0.5, 0.6, 0.7, 0.8, 0.9, 1.0, 1.25, 1.5, 1.75, 2.00 mm, or a tenth of any of those values, or $100^{th}$ of any of those values, or $1000^{th}$ of any of those values, of $10,000^{th}$ of any of those values from a distance of the surface of the electrode. In some embodiments, any of the teachings below can be executed to evaluate phenomenon associated with features falling within the aforementioned distances.

In some embodiments, as noted above, $Z_{e/t}$ is ignored. In some embodiments, this is because it is hard to interpret in determining proximity or perilymph/scalae impedance changes. However, $Z_{e/t}$ can provide useful information, in some embodiments, about the locality of any impedance change that may occur. In some embodiments, $Z_{e/t}$ provides a measure of the impedance at and very near to the metal contact of the stimulating electrode, and methods can include obtaining such estimate. This includes the so called 'metal/electrolyte' interface (a complex 'double layer' of charged particles within a nanometer or so of the metal electrode) and can also include, for example, in some embodiments, any perilymph and tissue in the immediate vicinity of the electrode contact. In some instances, in inorganic electrolytes, a so called "double layer" forms at the interface of the contact which is a few tenths of a nanometer (i.e. a few tenths of $10^{-9}$ meters) in thickness. This has impedance properties that resemble that of a capacitor. In the in-vivo environment, proteins also attached to the metal surface. These vary in thickness from a few nanometres to a few tens of nanometres, depending on the individual proteins and how they arrange themselves on the metal. Also, later cells, which are typically a few micrometers in diameter, attach to those proteins. Multiple layers of cells can form at these locations, leading to layers that are tens or hundreds of micrometers in thickness. All the above potentially contribute to $Z_{e/t}$. Thus, the teachings detailed herein can be used to identify the occurrence of one or more of these phenomenon (or at least determine that a deleterious condition exists, irrespective of its origin).

By measuring the voltage (or another electrical property/any electrical property that has utility can be used) on the stimulating electrode ($V_n$), a measure of $Z_{e/t}$ can be obtained. Note that $V_n/I_{stim}$ is not a direct measure of $Z_{e/t}$. It is not possible to get a value for $Z_{e/t}$ directly. However by subtracting the average value of the neighboring electrode voltages, the voltage of the stimulating electrode can be obtained, which can be referred to herein as $V_{e/t}$, which in practice is dominated by $Z_{e/t}$.

Thus, in an exemplary embodiment $$Z_{e/t} \sim \{V_n - [(V_{n+1} + V_{n-1})/2]\}/I_{stim}$$

Accordingly, in an exemplary embodiment, there is a method 1600 according to the algorithm of FIG. 16, wherein the method includes method action 1610, which includes applying an electrical current to an electrode located in a cochlea of a recipient, which electrode is a stimulating electrode. In an exemplary embodiment, the voltage is known/estimated, based on the current applied to the electrode. Thus, the method includes obtaining data indicative of an electrical property related to the stimulating electrode.

Method 1600 also includes method action 1620, which includes obtaining data indicative of respective electrical properties at at least two electrodes located away from the stimulating electrode. For example, this can be $V_{n+1}$ and $V_{n-1}$. In an exemplary embodiment, more than two electrodes can be utilized, e.g., $V_{n+1}$, $V_{n-1}$, $V_{n+2}$, $V_{n-2}$, etc. (and, can be averaged as seen above, thus expanding the above equation). Method 1600 also includes method action 1630, which includes determining an impedance related feature of the stimulating electrode. In an exemplary embodiment, action 1630 is executed by using the above equation. Thus, in an exemplary embodiment of method 1600, the action of determining the impedance related feature of the stimulating electrode includes subtracting an average of respective voltages at the at least two electrodes located away from the stimulating electrode from a voltage of the stimulating electrode and dividing the result by the current applied to the stimulating voltage.

Also, consistent with the teachings above, in an exemplary embodiment of method 1600, the action of determining an impedance related feature of the stimulating electrode is executed only by determining the feature indirectly.

In at least some exemplary embodiments, it is noted that proteins and the like that grow on the stimulating electrode or the other electrodes for that matter, may not result in a feature that can be identified when the skirt according to normal methods (e.g., where the features associated with a stimulating electrode are ignored). Conversely, by evaluating $Z_{e/t}$ according to the teachings detailed herein, if a change in $Z_{e/t}$ is identified, and nothing else has changed (e.g., the skirts remain identical/minimal difference over time), such can be inferred that proteins or the like is built up at the stimulating electrode. Alternatively, and/or in addition to this, other things can be inferred regarding the stimulating electrode. This can be utilized to evaluate whether or not action need be taken or otherwise whether or not it is utilitarian to take action to address phenomenon associated with the near space of the stimulating electrode. By way of example only and not by way of limitation, it might be utilitarian to explant the array in place a new array in the recipient. Alternatively, in an exemplary embodiment, that the channels associated with the electrode can be eliminated when the cochlear implant is utilized to evoke a hearing percept. Instead, the portions of the sound spectrum that would be normally applied to that channel can be placed on other channels or, those portions can simply be eliminated from the overall sound spectrum that is utilized to evoke a hearing percept.

Accordingly, at least some exemplary embodiments taken account the fact that interface impedance is different from bulk impedance. The teachings detailed herein can enable the identification of the interface impedance, and can enable the evaluation thereof to determine a phenomenon associated with the near space of the electrode.

The evaluation of $Z_{e/t}$/the tracking of $Z_{e/t}$ overtime can enable the determination of whether or not the electrode is functioning/whether or not the electrode is a viable electrode to be utilized to evoke a hearing percepts. In an exemplary embodiment, the evaluation/tracking of $Z_{e/t}$ can identify such phenomenon as, for example, the likelihood that delamination of a coating over the electrode has occurred. In an exemplary embodiment, an increase in current will result from this delamination. Accordingly, by analyzing the electrical data obtained from the teachings detailed herein, a determination can be made as to the likelihood of the occurrence of the delamination.

Figure 17:
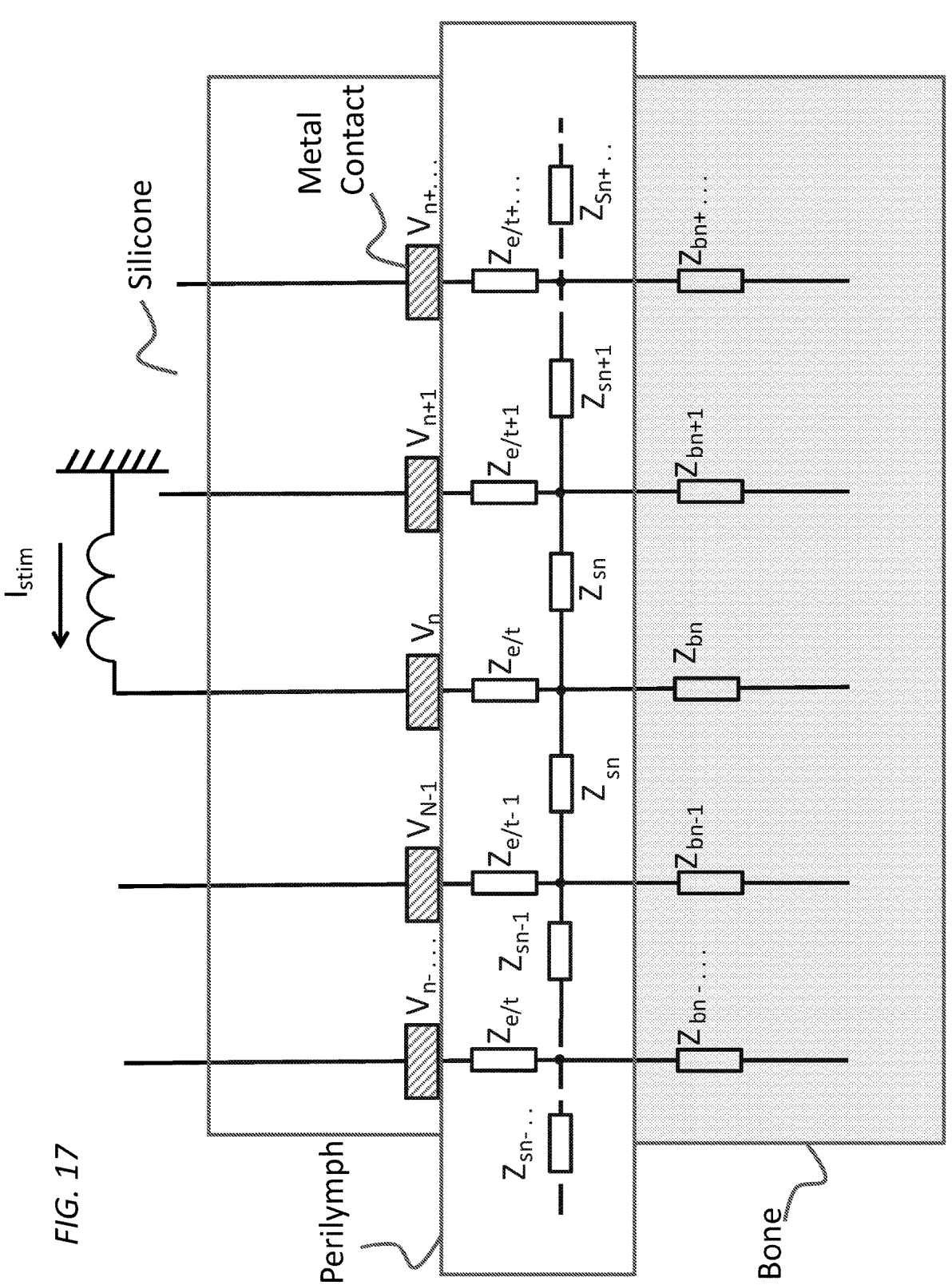
FIG. 17 presents a conceptual schematic applicable to the teachings herein.

FIG. 17 presents a more detailed view of the impedance network in FIG. 15, overlaid with the physical structures present (i.e. the silicone and metal of the electrode array, perilymph and bone). That is, FIG. 17 shows a schematic according to FIG. 15, but with physical features of the electrode and scala tympani indicated. $V_{e/t}$ can be measured for all electrodes and provides a more localized and precise measure of any impedance change and associated damage mechanisms local the electrode contact. This is in contrast to the previously described measures which are better at identifying impedance changes and associated damage mechanisms in the bulk of the scalae.

Thus, in view of the above, in an exemplary embodiment of the method 1600, the stimulating electrode is a metal contact, and the impedance related feature of the stimulating electrode is indicative of impedance at and proximate to the metal contact. In an exemplary embodiment, the impedance related feature of the stimulating electrode is indicative of impedance at and proximate to the metal contact and is indicative of the metal/electrolyte interface and perilymph and tissue in an immediate vicinity of the contact. In some embodiments, the impedance related feature of the stimulating electrode is impedance due to the electrode/tissue interface and the tissue and perilymph in the near vicinity of the stimulating electrode.

In an exemplary embodiment of method 1600, the method further includes determining whether a deleterious effect is occurring in the cochlea based on the determined impedance. By way of example only and not by way of limitation, a deleterious effect can be the growth of tissue, corrosion on a surface of the contact, movement of silicone over the contact, lack of perilymph in contact with the contact, etc. In view of the spatial dynamics of this embodiment, in exemplary embodiment of method 1600, the method further includes the action of comprising determining whether a deleterious effect is occurring in the cochlea in the immediate vicinity of the stimulating electrode based on the determined impedance.

Any disclosure herein of functionality and/or analysis and/or control corresponds to a disclosure of a general-purpose computer and/or a processor and/or a program consumer electronic device specifically configured utilizing circuitry or the like, whether by the application of hardware, firmware and/or software, that is configured to execute that functionality and/or analysis. By way of example only and not by way of limitation, a laptop computer utilizing the USB ports can communicate with a device that includes a power source or otherwise is configured to obtain or receive power from another power source, such as industrial power or household power or batteries, etc., or a device that receives power from the personal computer, which device includes electronic circuitry to communicate with an implantable component of a cochlear implant and provide instructions and/or power via a RF inductance link, and thus includes an RF inductor and an RF inductor antenna and the circuitry and components to convert signals received from the laptop or the like to output signals that will be provided to the inductance coil that will communicate with the implanted inductance coil so that the implantable component of the cochlear implant will be controlled or otherwise operated according to the teachings detailed herein. The device can receive signals from the implanted component and provide those signals to the computer, raw or in a modified form, such as via utilizing a digital to analog converter, or by utilizing circuitry, etc. in an exemplary embodiment, the device can be external component of the cochlear implant, such as external component 142, that has been programmed to control the implantable component and receive data there from. In an exemplary embodiment, the teachings detailed herein can be executed under the control of the external component, and the external component can log the data received from the implanted component and/or can communicate the data to a remote device, in real time or in batch indications, etc., where the data can be evaluated. Indeed, the external component can perform some of the evaluations. Such can have utilitarian value with respect to an autonomous device that performs the data acquisition methods herein while the recipient is sleeping for example, or while the recipient is going on with his or her life. In an exemplary embodiment, the method actions detailed herein can be executed, at least in part, autonomously, according to a preplanned regime, that is transparent or practically transparent to the recipient. The external component can be configured to analyze the data or otherwise simply pass on the data, where the data can be analyzed remotely or by another device, such as a smart phone in signal communication with the external component.

It is noted that any disclosure herein of functionality of the external component also corresponds to a disclosure of functionality of the implanted component, such as in in an embodiment where the cochlear implant is a fully implantable device.

Figure 18:
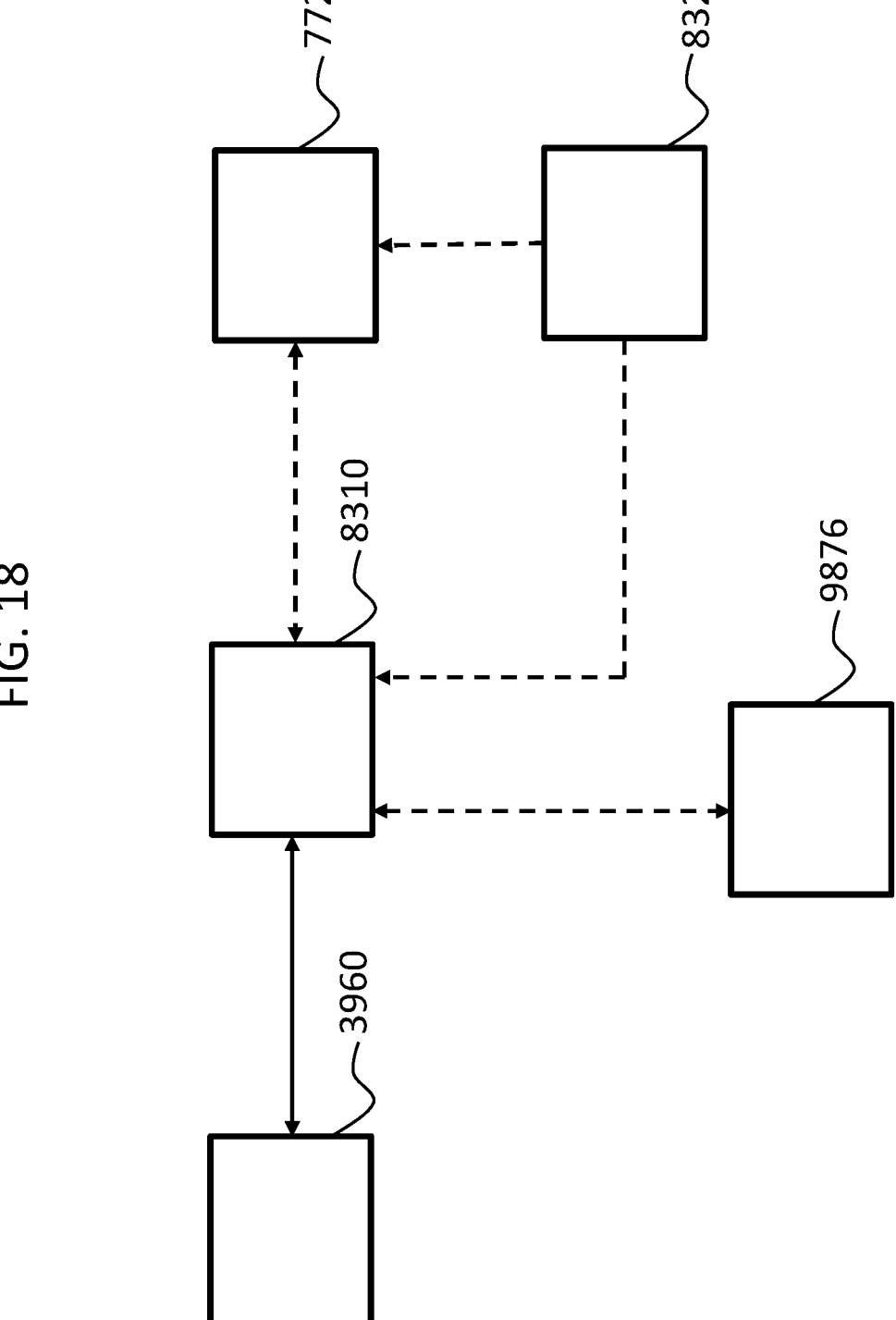
FIG. 18 depicts an exemplary functional diagram of an exemplary embodiment.

As can be recognized from the above, the electrode array can be utilized to obtain the data utilized in the methods herein, such as by way of example only and not by way of limitation, the voltages at the read electrodes, and can also be used to provide the stimulating electrode (just in case for some reason that was not clear). FIG. 18 depicts an exemplary system for utilizing the cochlear implant to obtain such information. Presented in functional terms, there is a test unit 3960 in signal communication with unit 8310, which in turn is in signal communication, optionally with a unit 7720 and a unit 8320, the details of which will be described below.

Figure 19:
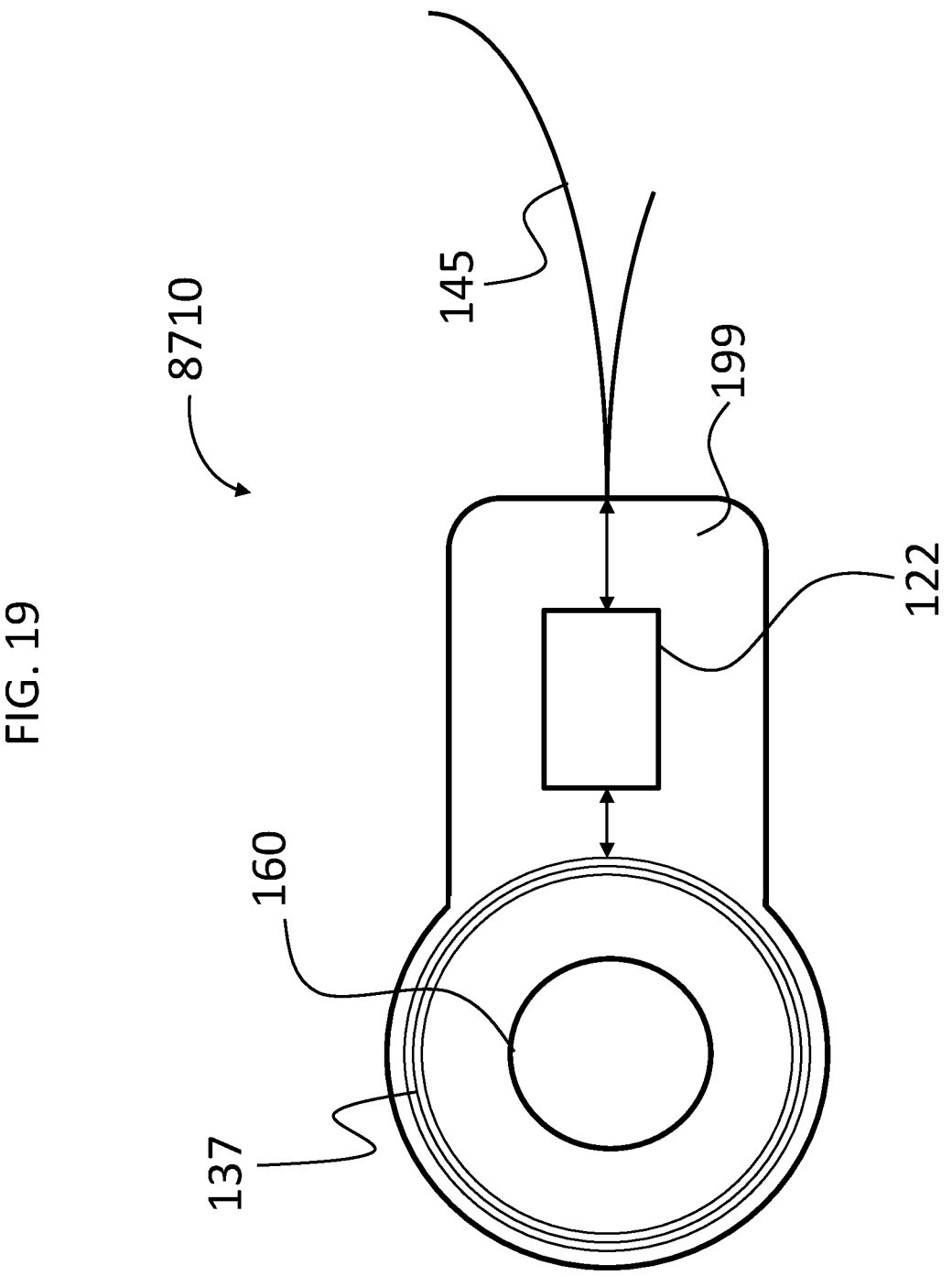
FIG. 19 depicts an exemplary implantable component of a cochlear implant according to an exemplary embodiment.

Unit 3960 can correspond to an implantable component of an electrode array, as seen in FIG. 1. More specifically, FIG. 19 depicts an exemplary high-level diagram of a receiver/stimulator 8710 (the implantable portion of 100) of a cochlear implant, looking downward. As can be seen, the receiver/stimulator 8710 includes a magnet 160 that is surrounded by a coil 137 that is in two-way communication (although in other embodiments, the communication is one-way) with a stimulator unit 122, which in turn is in communication with the electrode array 145. Receiver/stimulator 8710 further includes a cochlear stimulator unit 122, in signal communication with the coil 137. The coil 137 and the stimulator unit 122 are encased in silicon as represented by element 199. In an exemplary embodiment, receiver/stimulator 8710 is utilized as test unit 3960, and is used to acquire information about electrode array position.

Figure 20:
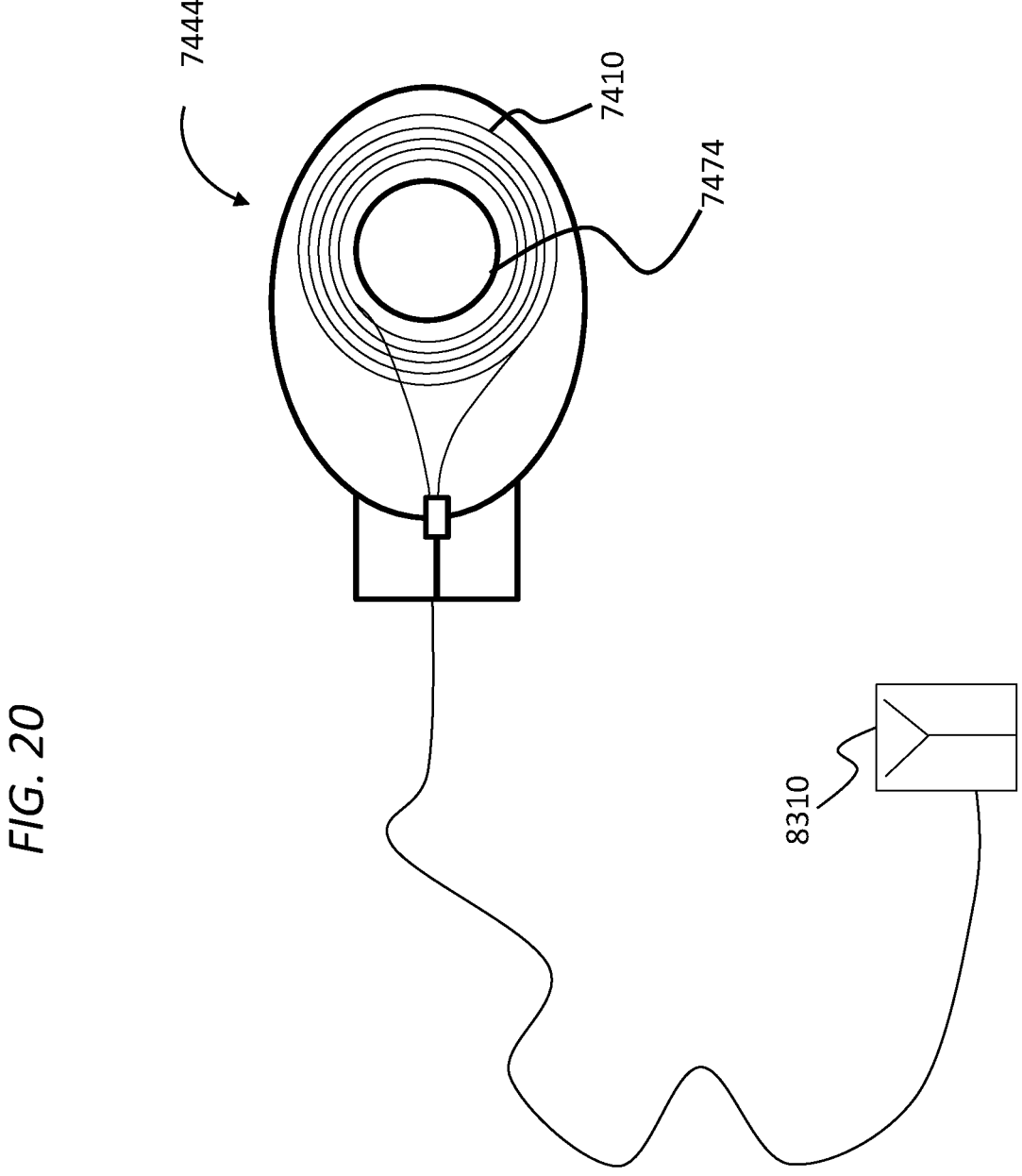
FIG. 20 depicts a component that places the cochlear implant of FIG. 8 into signal communication with another component.

FIG. 20 depicts an exemplary RS (receiver/stimulator) interface 7444 which is presented by way of concept. An inductance coil 7410 is configured to establish a magnetic inductance field so as to communicate with the corresponding coil of the receiver-stimulator of the cochlear implant. Interface 7444 includes a magnet 7474 so as to hold the inductance coil 7410 against the coil of the receiver/stimulator of the cochlear implant in a manner analogous to how the external component of the cochlear implant is held against the implanted component, and how the coils of those respective components are aligned with one another. As can be seen, an electrical lead extends from the coil 7410 to control unit 8310, representing signal communication between interface 7444, and control unit 8310.

Figure 21:
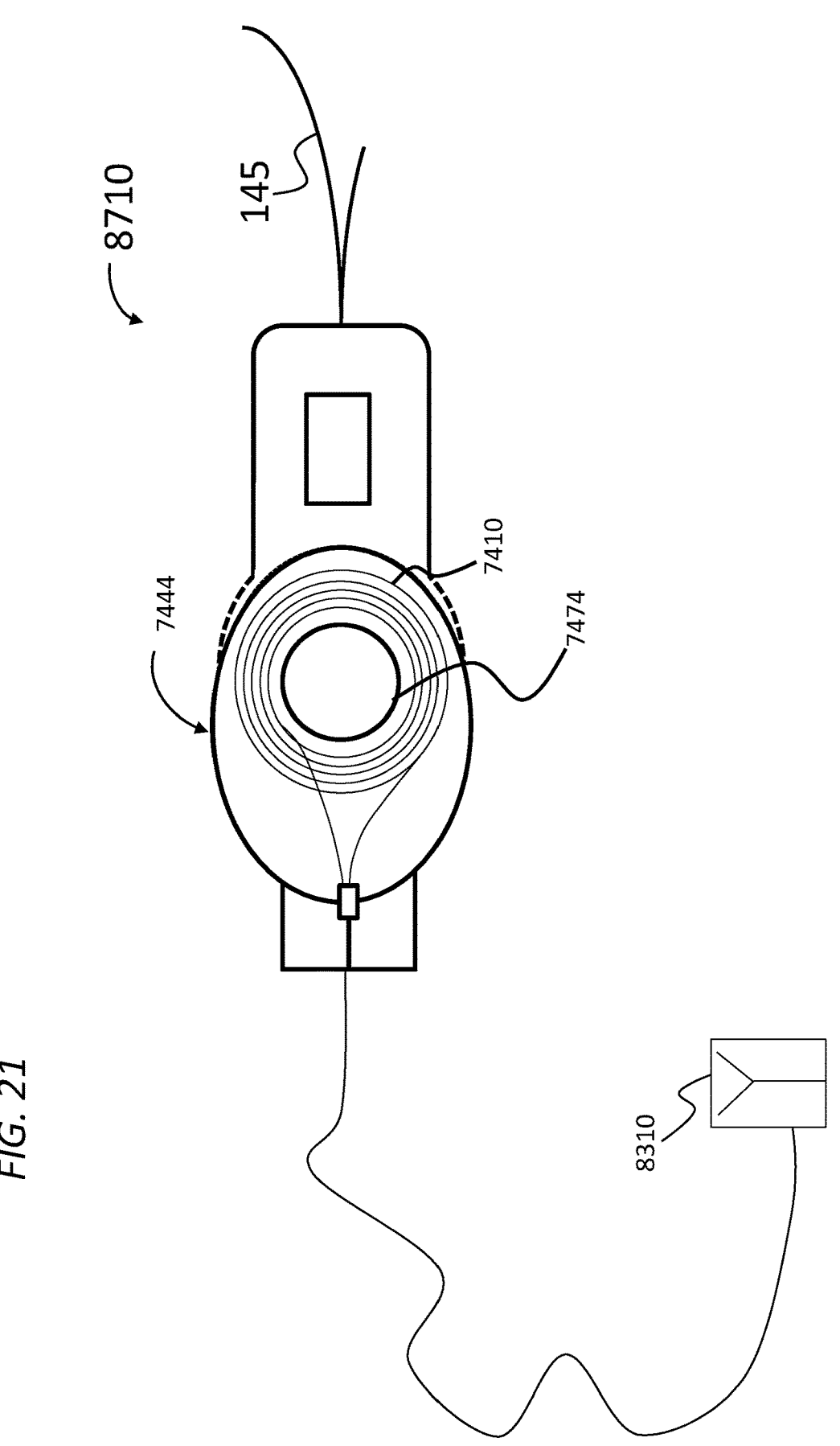
FIG. 21 depicts the cochlear implant in signal communication with a communication device that enables communication between the cochlear implant and a control unit according to an exemplary embodiment.

FIG. 21 depicts an exemplary embodiment of the receiver/stimulator 8710 in signal communication with the control unit 8310 via electrical lead that extends from the interface device 7444 having coil 7410 about a magnet 7474 as can be seen. The interface device 7444 communicates via an inductance field with the inductance coil of the receiver/stimulator 8710 so that the data acquired by the implantable component 8710 (receiver/stimulator) can be transferred to the control unit 8310.

Note also that in at least some alternate exemplary embodiments, control unit 8310 can communicate with the so-called "hard ball" reference electrode of the implantable component of the cochlear implant so as to enable communication of data from the receiver/stimulator 8710 to control unit 8310 and/or vice versa.

It is noted that in the embodiment of FIG. 21, control unit 8310 is in signal communication with the various other components as detailed herein, which components are not depicted in FIG. 21 for purposes of clarity.

Also functionally depicted in FIG. 18 is the optional embodiment where an electrode array insertion robotic system/actuator system 7720 and an input device 8320 is included in the system. In an exemplary embodiment, the input device 8320 could be a trigger of a hand held device that controls the actuator system 7720 and can stop and/or start insertion of the actuator. In an exemplary embodiment, the input device 8320 could be a trigger on the tool 8200.

Control unit 8310 can be a signal processor or the like or a personal computer or the like or a mainframe computer or the like etc., that is configured to receive signals from the test unit 3960 and analyze those signals to evaluate the data obtained (it can also be used to control the implant/control the application of current). More particularly, the control unit 8310 can be configured with software the like to analyze the signals from test unit 3960 in real time and/or in near real time as the electrode array is being advanced into the cochlea by actuator assembly 7720 (if present, and if not present, while the array is being inserted/advanced by hand). The control unit 8310 analyzes the input from test unit 3960, after partial and/or full implantation and/or after the surgery is completed and/or as the electrode array advanced by the actuator assembly 7720 and/or as the electrode array is advanced by the surgeon by hand. The controller/control unit can be programmed to also control the stimulation/control the providing of current to the electrodes during the aforementioned events/situations. The controller 8310 can evaluate the input to determine if there exists a phenomenon according to the teachings detailed herein. That said, in an alternate embodiment, or in addition to this, the controller 8310 can output a signal to an optional monitor 9876 or other output device (e.g., buzzer, light, etc.), that can provide the surgeon or other healthcare professional performing the operation or evaluating the data postoperatively, etc., indicative of the data obtained and/or indicative of a conclusion reached by the control unit 8310. Note also that in an exemplary embodiment, the control unit 8310 can be a dumb unit in the sense that it simply passes along signals to the implant (e.g., the control unit can instead be a series of, for example, buttons where a surgeon depression is one button to provide stimulation to a given electrode).

Still, in some embodiments, the control unit 8310 is configured or otherwise programmed to evaluate input and determine if the input indicates that the electrode array is positioned in a given manner were otherwise that the electrode array is positioned in a manner different than that which was desired. In an exemplary embodiment, upon such a determination, control unit 8310 could halt the advancement of the array into the cochlea by stopping the actuator(s) of actuator assembly 7720 and/or could slow the actuator(s) so as to slow rate of advancement of the electrode array into the cochlea and/or could reverse the actuator(s) so as to reverse or otherwise retract the electrode array within the cochlea (either partially or fully). Alternatively, in embodiments where actuator assembly 7720 is not present, control unit 8310 could provide an indication to the surgeon or the like (via an integrated component, such as a buzzer or a light on the control unit, or an LDC screen, or via device 9876) to halt and/or slow the insertion, etc. In at least some exemplary embodiments, control unit 8310 can be configured to override the input from input unit 8320 input by the surgeon or the user.

Some exemplary embodiments utilize the receiver/stimulator 8710 as a test unit 3910 that enables the action of obtaining the data and the action of providing current to the electrode, and/or any one or more of the method actions detailed herein. In an exemplary embodiment, the receiver/stimulator 8710 and/or control unit 3810 and/or actuator assembly 7720 and/or input device 8320 are variously utilized to execute one or more or all of the method actions detailed herein, alone or in combination with an external component of a cochlear implant, and/or with the interface 7444, which can be used after the receiver/stimulator 8710 is fully implanted in the recipient and the incision to implant such has been closed (e.g., days, weeks, months or years after the initial implantation surgery). The interface 7444 can be used to control the receiver/stimulator to execute at least some of the method actions detailed herein (while in some other embodiments, the receiver/stimulator can execute such in an autonomous or semi-autonomous manner, without being in communication with an external component) and/or can be used to obtain data from the receiver/stimulator after execution of such method actions.

More specifically, because the electrode array includes a plurality of electrodes (in some embodiments, 22 electrodes), many if not all of which can be individually used as sources and/or sinks and many if not all of which can be utilized as "read" electrodes, the techniques detailed herein can be applied utilizing a cochlear electrode array.

Any method action detailed herein corresponds to a disclosure of a device and/or a system for executing that method action. Any disclosure of any method of making an apparatus detailed herein corresponds to a resulting apparatus made by that method. Any functionality of any apparatus detailed herein corresponds to a method having a method action associated with that functionality. Any disclosure of any apparatus and/or system detailed herein corresponds to a method of utilizing that apparatus and/or system. Any feature of any embodiment detailed herein can be combined with any other feature of any other embodiment detailed herein providing that the art enables such, unless such is otherwise noted.

Any disclosure herein of a method of making a device herein corresponds to a disclosure of the resulting device. Any disclosure herein of a device corresponds to a disclosure of making such a device.

Any one or more elements or features disclosed herein can be specifically excluded from use with one or more or all of the other features disclosed herein.

While various embodiments of the present invention have been described above, it should be understood that they have been presented by way of example only, and not limitation. It will be apparent to persons skilled in the relevant art that various changes in form and detail can be made therein without departing from the scope of the invention.

What is claimed is:

1. A method, comprising:
applying at first and second temporal locations respective electrical currents to an electrode located in a cochlea of a recipient;
obtaining first and second data indicative of electrical properties at a plurality of locations away from the electrode, the first and second data corresponding to data obtained, respectively, at the first and second temporal locations; and
evaluating whether or not there is an existence of a temporal change in electrical conductivity between the electrode and the plurality of locations based on the obtained data, wherein
the temporal change in electrical conductivity is a change in a spatial derivative of voltage between locations of the plurality of locations.

2. The method of claim 1, further comprising:
determining whether or not a phenomenon exists inside the cochlea based on the evaluation.

3. The method of claim 1, wherein:
the temporal change in electrical conductivity is due to a change in resistivity of material in the scalae of the cochlea.

4. The method of claim 1, wherein:
the temporal change in electrical conductivity is due to a change in resistivity of perilymph in the cochlea.

5. The method of claim 1, further comprising:
determining that the temporal change has occurred;
determining the temporal length from before a beginning of the change to a point during and/or after the change; and
determining that damage has occurred within the cochlea based on the determined temporal length.

6. The method of claim 1, further comprising:
determining that the temporal change has occurred; and
providing the recipient with drugs based solely on the determination.

7. Method of claim 1, further comprising:
determining whether or not a phenomenon exists inside the cochlea based on the evaluation;
plotting the data indicative of electrical properties for the locations of the plurality of locations away from the electrode to obtain respective curves; and
determining whether or not a change of a slope in one or more of the respective curves has occurred to determine whether or not the phenomenon exists.

8. The method of claim 1, wherein:
a first location of the plurality of locations is on a first side of the electrode and a second location of the plurality of locations is on a second side of the electrode opposite the first side of the electrode.

9. A method, comprising:
applying an electrical current to an electrode located in a cochlea of a recipient;

obtaining data, based on measurements, indicative of electrical properties at a plurality of locations away from the electrode;
evaluating electrical conductivity between respective locations of the plurality of locations based on the obtained data to identify spatial derivatives between the respective locations of the plurality of locations; and
determining whether or not a phenomenon exists in the recipient based on the identified spatial derivatives between the respective locations of the plurality of locations.

10. The method of claim 9, wherein:
the action of determining whether or not a phenomenon exists in the recipient includes determining whether or not a phenomenon exists at boundarie(s) of the cochlea based on the evaluation.

11. The method of claim 10, wherein:
the phenomenon is one of:
a sealed cochlea at a location through which an electrode array assembly extends from outside the cochlea to inside the cochlea; or
a non-sealed cochlea or a partially sealed cochlea at the location through which the electrode array assembly extends from outside the cochlea to inside the cochlea.

12. The method of claim 10, wherein:
the action of applying electrical current and obtaining the data and evaluating is executed during a cochlear implant electrode array surgery; and
the method further includes adjusting a seal at a location through which the electrode array assembly of the cochlear implant extends from outside the cochlea to inside the cochlea based on the determination.

13. The method of claim 10, wherein:
the action of applying electrical current and obtaining the data and evaluating is executed during a cochlear implant electrode array surgery in real time during the surgery.

14. The method of claim 9, wherein:
the action of determining whether or not a phenomenon exists in the recipient includes determining that the phenomenon exists, and that the phenomenon is a localized phenomenon, wherein the method further includes determining a location of the localized phenomenon within the cochlea.

15. The method of claim 9, wherein:
the phenomenon is a completely sealed cochlea.

16. The method of claim 9, wherein:
the action of evaluating electrical conductivity results in determining values of the spatial derivatives between the respective locations of the plurality of locations; and
the action of determining whether or not the phenomenon exists in the recipient based on spatial derivatives between the respective locations of the plurality of locations includes determining that the phenomenon exists based on the values of the spatial derivatives between the respective locations of the plurality of locations.

17. The method of claim 9, wherein:
the spatial derivatives between the locations are spatial derivatives of voltage; and
the action of evaluating the electrical conductivity between the respective locations of the plurality of locations results in identification of the spatial derivatives of voltage.

18. The method of claim 9, wherein:
the electrical properties include voltage.

19. A method, comprising:
applying an electrical current to an electrode located in a cochlea of a recipient;
obtaining data indicative of electrical properties at a plurality of locations away from the electrode; and
determining a spatial locational feature of the electrode within the cochlea relative to an anatomical structure of the cochlea based on a gradient of the obtained electrical properties, wherein
the electrode is an electrode of an electrode array of a cochlear implant, and
at least one of:
    (i) the spatial locational feature is a classification of the electrode array positioning from a group consisting of modiolar positioning, central positioning and lateral positioning; or
    (ii) the method further comprises:
        comparing the gradient to a database of gradients; and
        based on the comparison, determining a position of the electrode array relative to a modiolus of the cochlea based on a steepness of the gradient relative to gradients of the database of gradients.

20. The method of claim 19, wherein:
the spatial locational feature is an evaluation of a proximity of the electrode to the modiolus of the cochlea.

21. The method of claim 19, wherein:
the plurality of locations are locations of other electrodes of the electrode array than the electrode to which current is applied; and the spatial locational feature is the classification of the electrode array positioning from the group consisting of modiolar positioning, central positioning and lateral positioning.

22. The method of claim 21, wherein:
the method further comprises comparing the gradient to a database of gradients; and
based on the comparison, determining that the electrode array is positioned in one of the three electrode array positioning classifications.

23. The method of claim 19, wherein:
the plurality of locations are locations of other electrodes of the electrode array other than that to which current is applied; and
the method further comprises:
    comparing the gradient to the database of gradients; and
    based on the comparison, determining the position of the electrode array relative to the modiolus of the cochlea based on the steepness of the gradient relative to gradients of the database of gradients.

24. The method of claim 19, wherein:
the plurality of locations are locations of other electrodes of the electrode array other than that to which current is applied; and
the action of applying electrical current and obtaining the data and determining the spatial locational feature is executed during a cochlear implant electrode array surgery in real time during the surgery.

25. The method of claim 19, wherein:
the plurality of locations are locations of other electrodes of the electrode array than the electrode to which current is applied.

* * * * *